(12) United States Patent
Hanash et al.

(10) Patent No.: US 12,405,274 B2
(45) Date of Patent: *Sep. 2, 2025

(54) METHODS FOR THE DETECTION AND TREATMENT OF LUNG CANCER

(71) Applicant: Board of Regents, The University of Texas System, Austin, TX (US)

(72) Inventors: Samir Hanash, Houston, TX (US); Ayumu Taguchi, Houston, TX (US); Ziding Feng, Houston, TX (US)

(73) Assignee: Board of Regents, The University of Texas System, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,506

(22) Filed: Mar. 28, 2023

(65) Prior Publication Data
US 2023/0314436 A1 Oct. 5, 2023

Related U.S. Application Data

(62) Division of application No. 16/484,177, filed as application No. PCT/US2018/017704 on Feb. 9, 2018.

(60) Provisional application No. 62/456,731, filed on Feb. 9, 2017.

(51) Int. Cl.
*G01N 33/574* (2006.01)
*G16B 5/20* (2019.01)

(52) U.S. Cl.
CPC . *G01N 33/57423* (2013.01); *G01N 33/57484* (2013.01); *G16B 5/20* (2019.02)

(58) Field of Classification Search
CPC .................. G01N 33/57423; G01N 33/57484
See application file for complete search history.

(56) References Cited

U.S. PATENT DOCUMENTS

| | | | |
|---|---|---|---|
| 2008/0133141 | A1 | 6/2008 | Frost |
| 2013/0196868 | A1 | 8/2013 | Lebowitz |
| 2014/0271453 | A1 | 9/2014 | Dowell |
| 2014/0274772 | A1 | 9/2014 | Borgia |
| 2015/0072890 | A1 | 3/2015 | James |
| 2016/0060329 | A1 | 3/2016 | Sin |
| 2020/0025766 | A1 | 1/2020 | Hanash |
| 2024/0159753 | A1* | 5/2024 | Hanash ............ G01N 33/57423 |

FOREIGN PATENT DOCUMENTS

| | | |
|---|---|---|
| CN | 102321760 | 1/2012 |
| WO | 2007076439 | 7/2007 |
| WO | 2008144034 | 11/2008 |
| WO | 2011140234 | 11/2011 |
| WO | 2011150974 | 12/2011 |
| WO | 2016205960 | 12/2016 |

(Continued)

OTHER PUBLICATIONS

Bach, P. et al., "Variations in Lung Cancer Risk Among Smokers", J Natl Cancer Inst., 95(6):470-8, (2003).

(Continued)

*Primary Examiner* — Diana B Johannsen
(74) *Attorney, Agent, or Firm* — Global Patent Group Inc.; Cynthia Hathaway; Michael Sertic

(57) ABSTRACT

Provided are methods and related kits for detection of early stage lung cancer, and determination of risk of harboring lung cancer.

5 Claims, 4 Drawing Sheets

Specification includes a Sequence Listing.

(56) References Cited

FOREIGN PATENT DOCUMENTS

| WO | 2017155570 | 9/2017 |
|---|---|---|
| WO | 2018148600 | 8/2018 |

OTHER PUBLICATIONS

Cassidy, A. et al., "The LLP Risk Model: An Individual Risk Prediction Model for Lung Cancer", Br J Cancer, 98 (2):270-6, (2008).

EP Patent Application No. 18752036.6; Third Party Observations under Article 115 EPC, dated Dec. 11, 2019; 3 pages.

Fahrmann, J. et al., "Blood-Based Biomarker Panel for Personalized Lung Cancer Risk Assessment", J Clin Oncol., 40(8):876-83, (2022).

Fernandez-Cuesta, L. et al., "Identification of Circulating Tumor DNA for the Early Detection of Small-Cell Lung Cancer", EBioMedicine, 10:117-23, (2016).

Hoggart, C. et al., "A Risk Model for Lung Cancer Incidence", Cancer Prev Res (Phila)., 5(6):834-46, (2012).

International Application No. PCT/US2018/017704; International Preliminary Report on Patentability, date of issuance Aug. 13, 2018; 34 pages.

International Application No. PCT/US2018/017704; International Search Report and Written Opinion of the International Searching Authority, date of mailing Apr. 27, 2018; 37 pages.

Jett, J. et al., "Audit of the Autoantibody Test, EarlyCDT-Lung, in 1600 Patients: An Evolution of It's Performance in Routine Clinical Practice", Lung Cancer, 83(1):51-5, (2014).

Johansson, M. et al., "Comprehensive Evaluation of Promising Biomarkers for Lung Cancer Risk Prediction", Cancer Res., 76(14):Abstract 2259, (2016).

Johansson, M., "Can Biomarkers be Used to Improve Risk Prediction Models on Lung Cancer?" IARC/WHO presentation, 38 pages, (2016).

Johansson, M., "Can Biomarkers be Used to Improve Risk Prediction Models on Lung Cancer?", Cancer Epidemiology, Biomarkers & Prevention, Abstract IA19, 4 pages, (2016).

Sequist, L. et al., "A New Era of Protein-Based Assays for Cancer Early Detection", J Thorac Oncol., 16(2):191-3, (2021).

Sin, D. et al., "Pro-Surfactant Protein B as a Biomarker for Lung Cancer Prediction", J Clin Oncol., 31(36):4536-43, (2013).

Sozzi, G. et al., "Clinical Utility of a Plasma-Based miRNA Signature Classifier Within Computed Tomography Lung Cancer Screening: A Correlative MILD Trial Study", J Clin Oncol., 32(8):768-73, (Mar. 10, 2014).

Spitz, M. et al., "An Expanded Risk Prediction Model for Lung Cancer", Cancer Prev Res (Phila)., 1(4):250-4, (2008).

U.S. Appl. No. 16/484,177; Non-Final Office Action, dated Dec. 22, 2022; 22 pages.

Wikoff, W. et al., "Diacetylspermine Is a Novel Prediagnostic Serum Biomarker for Non-Small-Cell Lung Cancer and Has Additive Performance With Pro-Surfactant Protein B", J Clin Oncol., 33(33):3880-6, (2015).

U.S. Appl. No. 16/484,177; Final Office Action, dated Aug. 10, 2023; 15 pages.

Cedrés, S. et al., "Serum tumor markers CEA, CYFRA21-1, and CA-125 are associated with worse prognosis in advanced non-small-cell lung cancer (NSCLC)", Clin Lung Cancer, 12(3):172-9, (2011).

Molina, R. et al., "Tumor markers (CEA, CA 125, CYFRA 21-1, SCC and NSE) in patients with non-small cell lung cancer as an aid in histological diagnosis and prognosis. Comparison with the main clinical and pathological prognostic factors", 24(4):209-18,(2003).

U.S. Appl. No. 16/484,177; Final Office Action, dated Nov. 4, 2024; 12 pages.

* cited by examiner

SEQUENCE LISTING

```
Sequence total quantity: 4
SEQ ID NO: 1                moltype = AA   length = 702
FEATURE                     Location/Qualifiers
source                      1..702
                            mol_type = protein
                            organism = Homo sapiens
SEQUENCE: 1
MESPSAPPHR WCIPWQRLLL TASLLTFWNP PTTAKLTIES TPFNVAEGKE VLLLVHNLPQ    60
HLFGYSWYKG ERVDGNRQII GYVIGTQQAT PGPAYSGREI IYPNASLLIQ NIIQNDTGFY   120
TLHVIKSDLV NEEATGQFRV YPELPKPSIS SNNSKPVEDK DAVAFTCEPE TQDATYLWWV   180
NNQSLPVSPR LQLSNGNRTL TLFNVTRNDT ASYKCETQNP VSARRSDSVI LNVLYGPDAP   240
TISPLNTSYR SGENLNLSCH AASNPPAQYS WFVNGTFQQS TQELFIPNIT VNNSGSYTCQ   300
AHNSDTGLNR TTVTTITVYA EPPKPFITSN NSNPVEDEDA VALTCEPEIQ NTTYLWWVNN   360
QSLPVSPRLQ LSNDNRTLTL LSVTRNDVGP YECGIQNKLS VDHSDPVILN VLYGPDDPTI   420
SPSYTYYRPG VNLSLSCHAA SNPPAQYSWL IDGNIQQHTQ ELFISNITEK NSGLYTCQAN   480
NSASGHSRTT VKTITVSAEL PKPSISSNNS KPVEDKDAVA FTCEPEAQNT TYLWWVNGQS   540
LPVSPRLQLS NGNRTLTLFN VTRNDARAYV CGIQNSVSAN RSDPVTLDVL YGPDTPIISP   600
PDSSYLSGAN LNLSCHSASN PSPQYSWRIN GIPQQHTQVL FIAKITPNNN GTYACFVSNL   660
ATGRNNSIVK SITVSASGTS PGLSAGATVG IMIGVLVGVA LI                     702
```

```
SEQ ID NO: 2           moltype = AA   length = 14451
FEATURE                Location/Qualifiers
source                 1..14451
                       mol_type = protein
                       organism = Homo sapiens
SEQUENCE: 2
MLKPSGLPGS SSPTRSLMTG SRSTKATPEM DSGLTGATLS PKTSTGAIVV TEHTLPFTSP    60
DKTLASPTSS VVGRTTQSLG VMSSALPEST SRGMTHSEQR TSPSLSPQVN GTPSRNYPAT   120
SMVSGLSSPR TRTSSTEGNF TKEASTYTLT VETTSGPVTE KYTVPTETST TEGDSTETPW   180
DTRYIPVKIT SPMKTFADST ASKENAPVSM TPAETTVTDS HTPGRTNPSF GTLYSSFLDL   240
SPKGTPNSRG ETSLELILST TGYPFSSPEP GSAGHSRIST SAPLSSSASV LDNKISETSI   300
FSGQSLTSPL SPGVPEARAS TMPNSAIPFS MTLSNAETSA ERVRSTISSL GTPSISTKQT   360
AETILTFHAF AETMDIPSTH IAKTLASEWL GSPGTLGGTS TSALTTTSPS TTLVSEETNT   420
HHSTSGKETE GTLNTSMTPL ETSAPGEESE MTATLVPTLG FTTLDSKIRS PSQVSSSHPT   480
RELRTTGSTS GRQSSSTAAH GSSDILRATT SSTSKASSWT SESTAQQFSE PQHTQWVETS   540
PSMKTERPPA STSVAAPITT SVPSVVSGFT TLKTSSTKGI WLEETSADTL IGESTAGPTT   600
HQFAVPTGIS MTGGSSTRGS QGTTHLLTRA TASSETSADL TLATNGVPVS VSPAVSKTAA   660
GSSPPGGTKP SYTMVSSVIP ETSSLQSSAF REGTSLGLTP LNTRHPFSSP EPDSAGHTKI   720
STSIPLLSSA SVLEDKVSAT STFSHHKATS SITTGTPEIS TKTKPSSAVL SSMTLSNAAT   780
SPERVRNATS PLTHPSPSGE ETAGSVLTLS TSAETTDSPN IHPTGTLTSE SSESPSTLSL   840
PSVSGVKTTF SSSTPSTHLF TSGEETEETS NPSVSQPETS VSRVRTTLAS TSVPTPVFPT   900
MDTWPTRSAQ FSSSHLVSEL RATSSTSVTN STGSALPKIS HLTGTATMSQ TNRDTFNDSA   960
APQSTTWPET SPRFKTGLPS ATTTVSTSAT SLSATVMVSK FTSPATSSME ATSIREPSTT  1020
ILTTETTNGP GSMAVASTNI PIGKGYITEG RLDTSHPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
TDRSLNTGVT RASRLENGSD TSSKSLSMGN STHTSMTYTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVSGLT  2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
VSLDNETTVK TSDILDARKT NELPSDSSSS SDLINTSIAS STMDVTKTAS ISPTSISGMT  2400
ASSSPSLFSS DRPQVPTSTT ETNATSPSV SSNTYSLDGG SNVGGTPSTL PPFTITHPVE  2460
TSSALLAWSR PVRTFSTMVS TDTASGENPT SSNSVVTSVP APGTWTSVGS TTDLPAMGFL  2520
KTSPAGEAHS LLASTIEPAT AFTPHLSAAV VTGSSATSEA SLLTTSESKA IHSSPQTPTT  2580
PTSGANWETS ATPESLLVVT ETSDTTLTSK ILVTDTILFS TVSTPPSKFP STGTLSGASF  2640
PTLLPDTPAI PLTATEPTSS LATSFDSTPL VTIASDSLGT VPETTLTMSE TSNGDALVLK  2700
TVSNPDRSIP GITIQGVTES PLHPSSTSPS KIVAPRNTTY EGSITVALST LPAGTTGSLV  2760
FSQSSSENSET TALVDSSAGL ERASVMPLTT GSQGMASSGG IRSGSTHSTG TKTFSSLPLT  2820
MNPGEVTAMS EITTNRLTAT QSTAPKGIPV KPTSAESGLL TPVSASSSPS KAFASLTTAP  2880
PTWGIPQSTL TFEFSEVPSL DTKSASLPTP GQSLNTIPDS DASTASSSLS KSPEKNPRAR  2940
MMTSTKAISA SSFQSTGFTE TPEGSASPSM AGHEPRVPTS GTGDPRYASE SMSYPDPSKA  3000
SSAMTSTSLA SKLTTLFSTG QAARSGSSSS PISLSTEKET SFLSPTASTS RKTSLFLGPS  3060
MARQPNILVH LQTSALTLSP TSTLNMSQEE PPELTSSQTI AEEEGTTAET QTLTFTPSET  3120
PTSLLPVSSP TEPTARRKSS PETWASSISV PAKTSLVETT DGTLVTTIKM SSQAAQGNST  3180
WPAPAEETGS SPAGTSPGSP EMSTTLKIMS SKEPSISPEI RSTVRNSPWK TPETTVPMET  3240
TVEPVTLQST ALGSGSTSIS HLPTGTTSPT KSPTENMLAT ERVSLSPSPP EAWTNLYSGT  3300
PGGTRQSLAT MSSVSLESPT ARSITGTGQQ SSPELVSKTT GMEFSMWHGS TGGTTGDTHV  3360
SLSTSSNILE DPVTSPNSVS SLTDKSKHKT ETWVSTTAIP TVLNNKIMA AEQQTSRSVD  3420
EAYSSTSSWS DQTSGSDITL GASPDVTNTL YITSTAQTTS LVSLPSGDQG ITSLTNPSGG  3480
KTSSASSVTS PSIGLETLRA NVSAVKSDIA PTAGHLSQTS SPAEVSILDV TTAPTPGIST  3540
TITTMGTNSI STTTPNPEVG MSTMDSTPAT ERRTTSTEHP STWSSTAASD SWTVTDMTSN  3600
LKVARSPGTI STMHTTSFLA SSTELDSMST PHGRITVIGT SLVTPSSDAS AVKTETSTSE  3660
RTLSPSDTTA STPISTFSRV QRMSISVPDI LSTSWTPSST EAEDVPVSMV STDHASKTD  3720
PNTPLSTFLF DSLSTLDWDT GRSLSSATAT TSAPQGATTP QELTLETMIS PATSQLPFSI  3780
GHITSAVTPA AMARSSGVTF SRPDPTSKKA EQTSTQLPTT TSAHPGQVPR SAATTLDVIP  3840
HTAKTPDATF QRQGQTALTT EARATSDSWN EKEKSTPSAP WITEMMNSVS EDTIKEVTSS  3900
SSVLRTLNTL DINLESGTTS SPSWKSSPYE RIAPSESTTD KEAIHPSTNT VETTGWVTSS  3960
EHASHSTIPA HSASSKLTSP VVTTSTREQA IVSMSTTTWP ESTRARTEPN SFLTIELRDV  4020
SPYMDTSSTT QTSIISSPGS TAITKGPRTE ITSSKRISS FLAQSMRSSD SPSEAITRLS  4080
NFPPAMTESGG MILAMQTSPP GATSLSAPTL DTSATASWTG TPLATTQRFT YSEKTTLFSK  4140
GPEDTSQPSP PSVEETSSSS SLVPIHATTS PSNILLTSQG HSPSSTPPVT SVFLSETSGL  4200
GKTTDMSRIS LEPGTSLPPN LSSTAGEALS TYEASRDTKA IHHSADTAVT NMEATSSEYS  4260
PIPGHTKPSK ATSPLVTSHI MGDITSSTSV FGSSETTEIE TVSSVNQGLQ ERSTSQVASS  4320
ATETSTVITH VSSGDATTHV TKTQATFSSG TSISSPHQFI TSTNTFTDVS TNPSTSLIMT  4380
```

```
ESSGVTITTQ TGPTGAATQG PYLLDTSTMP YLTETPLAVT PDFMQSEKTT LISKGPKDVS    4440
WTSPPSVAET SYPSSLTPFL VTTIPPATST LQGQHTSSPV SATSVLTSGL VKTTDMLNTS    4500
MEPVTNSPQN LNNPSNEILA TLAATTDIET IHPSINKAVT NMGTASSAHV LHSTLPVSSE    4560
PSTATSPMVP ASSMGDALAS ISIPGSETTD IEGEPTSSLT AGRKENSTLQ EMNSTTESNI    4620
ILSNVSVGAI TEATKMEVPS FDATFIPTPA QSTKFPDIFS VASSRLSNSP PMTISTHMTT    4680
TQTGSSGATS KIPLALDTST LETSAGTPSV VTEGFAHSKI TTAMNNDVKD VSQTNPPFQD    4740
EASSPSSQAP VLVTTLPSSV AFTPQWHSTS SPVSMSSVLT SSLVKTAGKV DTSLETVTSS    4800
PQSMSNTLDD ISVTSAATTD IETTHPSINT VVTNVGTTGS AFESHSTVSA YPEPSKVTSP    4860
NVTTSTMEDT TISRSIPKSS KTTRTETETT SSLTPKLRET SISQEITSST ETSTVPYKEL    4920
TGATTEVSRT DVTSSSSTSF PGPDQSTVSL DISTETNTRL STSPIMTESA EITITTQTGP    4980
HGATSQDTFT MDPSNTTPQA GIHSAMTHGF SQLDVTTLMS RIPQDVSWTS PPSVDKTSSP    5040
SSFLSSPAMT TPSLISSTLP EDKLSSPMTS LLTSGLVKIT DILRTRLEPV TSSLPNFSST    5100
SDKILATSKD SKDTKEIFPS INTEETNVKA NNSGHESHSP ALADSETPKA TTQMVITTTV    5160
GDPAPSTSMP VHGSSETTNI KREPTYFLTP RLRETSTSQE SSFPTDTSFL LSKVPTGTIT    5220
EVSSTGVNSS SKISTPDHDK STVPPDTFTG EIPRVFTSSI KTKSAEMTIT TQASPPESAS    5280
HSTLPLDTST TLSQGGTHST VTQGFPYSEV TTLMGMGPGN VSWMTTPPVE ETSSVSSLMS    5340
SPAMTSPSPV SSTSPQSIPS SPLPVTALPT SVLVTTTDVL GTTSPESVTS SPPNLSSITH    5400
ERPATYKDTA HTEAAMHHST NTAVTNVGTS GSGHKSQSSV LADSETSKAT PLMSTTSTLG    5460
DTSVSTSTPN ISQTNQIQTE PTASLSPRLR ESSTSEKTSS TTETNTAFSY VPTGAITQAS    5520
RTEISSSRTS ISDLDRPTIA PDISTGMITR LFTSPIMTKS AEMTVTTQTT TPGATSQGIL    5580
PWDTSTTLFQ GGTHSTVSQG FPHSEITTLR SRTPGDVSWM TTPPVEETSS GFSLMSPSMT    5640
SPSPVSSTSP ESIPSSPLPV TALLTSVLVT TTNVLGTTSP EPVTSSPPNL SSPTQERLTT    5700
YKDTAHTEAM HASMHTNTAV ANVGTSISGH ESQSSVPADS HTSKATSPMG ITFAMGDTSV    5760
STSTPAFFET RIQTESTSSL IPGLRDTRTS EEINTVTETS TVLSEVPTTT TTEVSRTEVI    5820
TSSRTTISGP DHSKMSPYIS TETITRLSTF PFVTGSTEMA ITNQTGPIGT ISQATLTLDT    5880
SSTASWEGTH SPVTQRFPHS EETTTMSRST KGVSWQSPPS VEETSSPSSP VPLPAITSHS    5940
SLYSAVSGSS PTSALPVTSL LTSGRRKTID MLDTHSELVT SSLPSASSFS GEILTSEAST    6000
NTETIHFSEN TAETNMGTTN SMHKLHSSVS IHSQPSGHTP PKVTGSMMED AIVSTSTPGS    6060
PETKNVDRDS TSPLTPELKE DSTALVMNST TESNTVFSSV SLDAATEVSR AEVTYYDPTF    6120
MPASAQSTKS PDISPEASSS HSNSPPLTIS THKTIATQTG PSGVTSLGQL TLDTSTIATS    6180
AGTPSARTQD FVDSETTSVM NNDLNDVLKT SPFSAEEANS LSSQAPLLVT TSPSPVTSTL    6240
QEHSTSSLVS VTSVPTPTLA KITDMDTNLE PVTRSPQNLR NTLATSEATT DTHTMHPSIN    6300
TAVANVGTTS SPNEFYFTVS PDSDPYKATS AVVITSTSGD SIVSTSMPRS SAMKKIESET    6360
TFSLIFRLRE TSTSQKIGSS SDTSTVFDKA FTAATTEVSR TELTSSSRTS IQGTEKPTMS    6420
PDTSTRSVTM LSTFAGLTKS EERTIATQTG PHRATSQGTL TWDTSITTSQ AGTHSAMTHG    6480
FSQLDLSTLT SRVPEYISGT SPPSVEKTSS SSSLLSLPAI TSPSPVPTTL PESRPSSPVH    6540
LTSLPTSGLV KTTDMLASVA SLPPNLGSTS HKIPTTSEDI KDTEKMYPST NIAVTNVGTT    6600
TSEKESYSSV PAYSEPPKVT SPMVTSFNIR DTIVSTSMPG SSEITRIEME STFSLAHGLK    6660
GTSTSQDPIV STEKSAVLHK LTTGATETSR TEVASSRRTS IPGPDHSTES PDISTEVIPS    6720
LPISLGITES SNMTIITRTG PPLGSTSQGT FTLDTPTTSS RAGTHSMATQ EFPHSEMTTV    6780
MNKDPEILSW TIPPSIEKTS FSSSLMPSPA MTSPPVSSTL PKTIHTTPSP MTSLLTPSLV    6840
MTTDLTGTSP EPTTSSPPNL SSTSHEILTT DEDTTAIEAM HPSTSTAATN VETTSSGHGS    6900
QSSVLADSEK TKATAPMDTT STMGHTTVST SMSVSSETTK IKRESTYSLT PGLRETSISQ    6960
NASFSTDTSI VLSEVPTGTT AEVSRTEVTS SGRTSIPGPS QSTVLPEIST RTMTRLFASP    7020
TMTESAEMTI PTQTGPSGST SQDTLTLDTS TTKSQAKTHS TLTQRFPHSE MTTLMSRGPG    7080
DMSWQSSPSL ENPSSLPSLL SLPATTSPPP ISSTLPVTIS SSPLPVTSLL TSSPVTTTDM    7140
LHTSPELVTS SPPKLSHTSD ERLTTGKDTT NTEAVHPSTN TAASNVEIPS SGHESPSSAL    7200
ADSETSKATS PMFITSTQED TTVAISTPHF LETSSRIQKES ISSLSPKLRE TGSSVETSSA    7260
IETSAVLSEV SIGATTEISR TEVTSSSSRTS ISGGSAESTML PEISTTRKII KFPTSPILAE    7320
SSEMTIKTQT SPPGSTSEST FTLDTSTTPS LVITHSTMTQ RLPHSEITTL VSRGAGDVPR    7380
PSSLPVEETS PPSSQLSLSA MISPSPVSST LPASSHSSVA SVTSLLTPGQ VKTTEVLDSA    7440
AEPETSSPPS LSSTSVEILA TSEVTTDTEK IHPFSNTAVT KVGTSSSGHE SPSSVLPDSE    7500
TTKATSAMGT ISIMGDTSVS TLTPALSNTR KIQSEPASSL TTRLRETSTS EETSLATEAN    7560
TVLSKVSTGA TTEVSRTEAI SFSRTSMSGP EQSTMSQDIS IGTIPRISAS SVLTESAKMT    7620
ITTQTGPSES TLESTLNLNT ATTPSWVETH SIVIQGFPHP EMTTSMGRGP GGVSWPSSPPF    7680
VKETSPPSSP LSLPAVTSPH PVSTTFLAHI PPSPLPVTSL LTSGPATTTD ILGTSTEPGT    7740
SSSSSLSTTS HERLTTYKDT AHTEAVHPST NTGGTNVATT SSGYKSQSSV LADSSPMCTT    7800
STMGDTSVLT STPAFLETRR IQTELASSLT PGLRESSGSE GTSSGTKMST VLSKVPTGAT    7860
TEISKEDVTS IPGPAQSTIS PDISTRTVSW FSTSPVMTES AEITMNTHTS PLGATTQGTS    7920
TLDTSSTTSL TMTHSTISQG FSHSQMSTLM RRGPEDVSWM SPPLLEKTRP SFSLMSSPAT    7980
TSPSPVSSTL PESISSSPLP VTSLLTSGLA KTTDMLHKSS EPVTNSPANL SSTSVEILAT    8040
SEVTTDTEKT HPSSNRTVTD VGTSSSGHES TSFVLADSQT SKVTSPMVIT STMEDTSVST    8100
STPGFFETSR IQTEPTSSLT LGLRKTSSSE GTSLATEMST VLSGVPTGAT AEVSRTEVTS    8160
SSRTSISGFA QLTVSPETST ETITRLPTSS IMTESAEMMI KTQTDPPGST PESTHTVDIS    8220
TTPNWVETHS TVTQRFSHSE MTTLVSRSPG DMLWPSQSSV EETSSASSLL SLPATTSPSP    8280
VSSTLVEDFP SASLPVTSLL NPGLVITTDR MGISREPGTS STSNLSSTSH ERLTTLEDTV    8340
DTEDMQPSTH TAVTNVRTSI SGHESQSSVL SDSETPKATS PMGTTYTMGE TSVSISTSDF    8400
FETSRIQIEP TSSLTSGLRE TSSSERISSA TEGSTVLSEV PGATTEVSR TEVISSRGTS    8460
MSGPDQFTIS PDISTEAITR LSTSPIMTES AESAITIETG SPGATSEGTL TLDTSTTTFW    8520
SGTHSTASPG FSHSEMTTLM SRTPGDVPWP SLPSVEEASS VSSSLSSPAM TSTSFFSTLP    8580
ESISSSPHPV TALLTLGPVK TTDMLRTSSE PETSSPPNLS STSAEILATS EVTKDREKIH    8640
PSSNTPVVNV GTVIYKHLSP SSVLADLVTT KPTSPMATTS TLGNTSVSTS TPAFPETMMT    8700
QPTSSLTSGL REISTSQETS SATERSASLS GMPTGATTKV SRTEALSLGR TSTPGPAQST    8760
ISPEISTETI TRISTPLTTT GSAEMTITPK TGHSGASSQG TFTLDTSSRA SWPGTHSAAT    8820
HRSPHSGMTT PMSRGPEDVS WPSRPSVEKT SPPSSLVSLS AVTSPSPLYS TPSESSHSSP    8880
LRVTSLFTPV MMKTTDMLDT SLEPVTTSPP SMNITSDESL ATSKATMETE AIQLSENTAV    8940
TQMGTISARQ EFYSSYPGLP EPSKVTSPVV TSSTIKDIVS TTIPASSEIT RIEMESTSTL    9000
TPTPRETSTS QEIHSATKPS TVPYKALTSA TIEDSMTQVM SSSRGPSPDQ STMSQDISTE    9060
VITRLSTSPI KTESTEMTIT TQTGSPGATS RGTLTLDTST TFMSGTHSTA SQGFSHSQMT    9120
```

```
ALMSRTPGDV PWLSHPSVEE ASSASFSLSS PVMTSSSPVS STLPDSIHSS SLPVTSLLTS    9180
GLVKTTELLG TSSEPETSSP PNLSSTSAEI LAITEVTTDT EKLEMTNVVT SGYTHESPSS    9240
VLADSVTTKA TSSMGITYPT GDTNVLTSTP AFSDTSRIQT KSKLSLTPGL METSISEETS    9300
SATEKSTVLS SVPTGATTEV SRTEAISSSR TSIPGPAQST MSSDTSMETI TRISTPLTRK    9360
ESTDMAITPK TGPSGATSQG TFTLDSSSTA SWPGTHSATT QRFPQSVVTT PMSRGPEDVS    9420
WPSPLSVEKN SPPSSLVSSS SVTSPSPLYS TPSGSSHSSP VPVTSLFTSI MMKATDMLDA    9480
SLEPETTSAP NMNITSDESL AASKATTETE AIHVFENTAA SHVETTSATE ELYSSSPGFS    9540
EPTKVISPVV TSSSIRDNMV STTMPGSSGI TRIEIESMSS LTPGLRETRT SQDITSSTET    9600
STVLYKMPSG ATPEVSRTEV MPSSRTSIPG PAQSTMSLDI SDEVVTRLST SPIMTESAEI    9660
TITTQTGYSL ATSQVTLPLG TSMTFLSGTH STMSQGLSHS EMTNLMSRGP ESLSWTSPRF    9720
VETTRSSSSL TSLPLTTSLS PVSSTLLDSS PSSPLPVTSL ILPGLVKTTE VLDTSSEPKT    9780
SSSPNLSSTS VEIPATSEIM TDTEKIHPSS NTAVAKVRTS SSVHESHSSV LADSETTITI    9840
PSMGITSAVD DTTVFTSNPA FSETRRIPTE PTFSLTPGFR ETSTSEETTS ITETSAVLYG    9900
VPTSATTEVS MTEIMSSNRI HIPDSDQSTM SPDIITEVIT RLSSSSMMSE STQMTITTQK    9960
SSPGATAQST LTLATTTAPL ARTHSTVPPR FLHSEMTTLM SRSPENPSWK SSLFVEKTSS   10020
SSSSLLSLPVT TSPSVSSTLP QSIPSSSFSV TSLLTPGMVK TTDTSTEPGT SLSPNLSGTS   10080
VEILAASEVT TDTEKIHPSS SMAVTNVGTT SSGHELYSSV SIHSEPSKAT YPVGTPSSMA   10140
ETSISTSMPA NFETTGFEAE PFSHLTSGFR KTNMSLDTSS VTPTNTPSSP GSTHLLQSSK   10200
TDFTSSAKTS SPDWPPASQY TEIPVDIITP FNASPSITES TGITSFPESR FTMSVTESTH   10260
HLSTDLLPSA ETISTGTVMP SLSEAMTSFA TTGVPRAISG SGSPFSRTES GPGDATLSTI   10320
AESLPSSTPV PFSSSTFTTT DSSTIPALHE ITSSSATPYR VDTSLGTESS TTEGRLVMVS   10380
TLDTSSQPGR TSSSPILDTR MTESVELGTV TSAYQVPSLS TRLTRTDGIM EHITKIPNEA   10440
AHRGTIRPVK GPQTSTSPAS PKGLHTGGTK RMETTTTALK TTTTALKTTS RATLTTSVYT   10500
PTLGTLTPLN ASMQMASTIP TEMMITTPYV FPDVPETTSS LATSLGAETS TALPRTTPSV   10560
FNRESETTAS LVSRSGAERS PVIQTLDVSS SEPDTTASWV IHPAETIPTV SKTTPNFFHS   10620
ELDTVSSTAT SHGADVSSAI PTNISPSELD ALTPLVTISG TDTSTTFPTL TKSPHETETR   10680
TTWLTHPAET SSTIPRTIPN FSHHESDATP SIATSPGAET SSAIPIMTVS PGAEDLVTSQ   10740
VTSSGTDRNM TIPTLTLSPG EPKTIASLVT HPEAQTSSAI PTSTISPAVS RLVTSMVTSL   10800
AAKTSTTNRA LTNSPGEPAT TVSLVTHPAQ TSPTVPWTTS IFFHSKSDTT PSMTTSHGAE   10860
SSSAVPTPTV STEVPGVVTP LVTSSRAVIS TTIPILTLSP GEPETTPSMA TSHGEEASSA   10920
IPTPTVSPGV PGVVTSLVTS SRAVTSTTIP ILTFSLGEPE TTPSMATSHG TEAGSAVPTV   10980
LPEVPGMVTS LVASSRAVTS TTLPTLTLSP GEPETTPSMA TSHGAEASST VPTVSPEVPG   11040
VVTSLVTSSS GVNSTSIPTL ILSPGELETT PSMATSHGAE ASSAVPTPTV SPGVSGVVTP   11100
LVTSSRAVTS TTIPILTLSS SEPETTPSMA TSHGVEASSA VLTVSPEVPG MVTSLVTSSR   11160
AVTSTTIPTL TISSDEPETT TSLVTHSEAK MISAIPTLAV SPTVQGLVTS LVTSSGSETS   11220
AFSNLTVASS QPETIDSWVA HPGTEASSVV PTLTVSTGEP FTNISLVTHP AESSSTLPRT   11280
TSRFSHSELD TMPSTVTSPE AESSSAISTT ISPGIPGVLT SLVTSSGRDI SATFPTVPES   11340
PHESEATASW VTHPAVTSTT VPRTTPNYSH SEPDTTPSIA TSPGAEATSD FPTITVSPDV   11400
PDMVTSQVTS SGTDTSITIP TLTLSSGEPE TTTSFITYSE THTSSAIPTL PVSPGASKML   11460
TSLVISSGTD STTTFPTLTE TPYEPETTAI QLIHPAETNT MVPRTTPKFS HSKSDTTLPV   11520
AITSPGPEAS SAVSTTTISP DMSDLVTSLV PSSGTDTSTT FPTLSETPYE PETTATWLTH   11580
PAETSTTVSG TIPNFSHRGS DTAPSMVTSP GVDTRSGVPT TTIPPSIPGV VTSQVTSSAT   11640
DTSTAIPTLT PSPGEPETTA SSATHPGTQT GFTVPTRTVP SSEPDTMASW VTHPPQTSTP   11700
VSRTTSSFSH SSPDATTPVMA TSPRTEASSA VLTTISPGAP EMVTSQITSS GAATSTTVPT   11760
LTHSPGMPET TALLSTHPRT ETSKTFPAST VFPQVSETTA SLTIRPGAET STALPTQTTS   11820
SLFTLLVTGT SRVDLSPTAS PGVSAKTAPL STHPGTETST MIPTSTLSLG LLETTGLLAT   11880
SSSAETSTST LTLTVSPAVS GLSSASITTD KPQTVTSVTS ETTSPSVTSV PPEFSRTVTG   11940
TTMTLIPSEM PTPPKTSHGE GVSPTTILRT TMVEATNLAT TGSSPTVAKT TTTFNTLAGS   12000
LFTPLTTPGM STLASESVTS RTSYNHRSWI STTSSYNRRY WTPATSTPVT STFSPGISTS   12060
SIPSSTAATV PFMVPFTLNF TITNLQYEED MRHPGSRKFN ATERELQGLL KPLFRNSSLE   12120
YLYSGCRLAS LRPEKDSSAT AVDAICTHRP DPEDLGLDRE RLYWELSNLT NGIQELGPYT   12180
LDRNSLYVNG FTHRSSMPTT STPGTSTVDV GTSGTPSSSP SPTTAGPLLM PFTLNFTITN   12240
LQYEEDMRRT GSRKFNTMES VLQGLLKPLF KNTSVGPLYS GCRLTLLRPE KDGAATGVDA   12300
ICTHRLDPKS PGLNREQLYW ELSKLTNDIE ELGPYTLDRN SLYVNGFTHQ SSVSTTSTPG   12360
TSTVDLRTSG TPSSLSSPTI MAAGPLLVPF TLNFTITNLQ YGEDMGHPGS RKFNTTERVL   12420
QGLLGPIFKN TSVGPLYSGC RLTSLRSEKD GAATGVDAIC IHHLDPKSPG LNRERLYWEL   12480
SQLTNGIKEL GPYTLDRNSL YVNGFTHRTS VPTSSTPGTS TVDLGTSGTP FSLPSPATAG   12540
PLLVLFTLNF TITNLKYEED MHRPGSRKFN TTERVLQTLL GPMFKNTSVG LLYSGCRLTL   12600
LRSEKDGAAT GVDAICTHRL DPKSPGVDRE QLYWELSQLT NGIKELGPYT LDRNSLYVNG   12660
FTHWIPVPTS STPGTSTVDL GSGTPSSLPS PTTAGPLLVP FTLNFTITNL KYEEDMHCPG   12720
SRKFNTTERV LQSLLGPMFK NTSVGPLYSG CRLTLLRSEK DGAATGVDAI CTHRLDPKSP   12780
GVDREQLYWE LSQLTNGIKE LGPYTLDRNS LYVNGFTHQT SAPNTSTPGT STVDLGTSGT   12840
PSSLPSPTSA GPLLVPFTLN FTITNLQYEE DMHHPGSRKF NTTERVLQGL LGPMFKNTSV   12900
GLLYSGCRLT LLRPEKNGAA TGMDAICSHR LDPKSPGLNR EQLYWELSQL THGIKELGPY   12960
TLDRNSLYVN GFTHRSSVAP TSTPGTSTVD LGTSGTPSSL PSPTTAVPLL VPFTLNFTIT   13020
NLQYGEDMRH PGSRKFNTTE RVLQGLLGPL FKNSSVGPLY SGCRLISLRS EKDGAATGVD   13080
AICTHHLNPQ SPGLDREQLY WQLSQMTNGI KELGPYTLDR NSLYVNGFTH RSSGLTTSTP   13140
WTSTVDLGTS GTPSPVPSPT TTGPLLVPFT LNFTITNLQY EENMGHPGSR KFNITESVLQ   13200
GLLKPLFKST SVGPLYSGCR LTLLRPEKDG VATRVDAICT HRPDPKIPGL DRQQLYWELS   13260
QLTHSITELG PYTLDRDSLY VNGFTQRSSV PTTSTPGTFT VQPETSETPS SLPGPTATGP   13320
VLLPFTLNFT ITNLQYEEDM RRPGSRKFNT TERVLQGLLM PLFKNTSVSS LYSGCRLTLL   13380
RPEKDGAATR VDAVCTHRPD PKSPGLDRER LYWKLSQLTH GITELGPYTL DRHSLYVNGF   13440
THQSSMTTTR TPDTSTMHLA TSRTPASLSG PMTASPLLVL FTINFTITNL RYEENMHHPG   13500
SRKFNTTERV LQGLLRPVFK NTSVGPLYSG CRLTLLRPKK DGAATKVDAI CTYRPDPKSP   13560
GLDREQLYWE LSQLTHSITE LGPYTLDRDS LYVNGFTQRS SVPTTSIPGT PTVDLGTSGT   13620
PVSKPGPSAA SPLLVFTLN FTITNLQYEE NMQHPGSRKF NTTERVLQGL LRSLFKSTSV   13680
GPLYSGCRLT LLRPEKDGTA TGVDAICTHH PDPKSPRLDR EQLYWELSQL THNITELGPY   13740
ALDNDSLFVN GFTHRSSVST TSTPGTPTVY LGASKTPASI FGPSAASHLL ILFTLNFTIT   13800
NLRYEENMWP GSRKFNTTER VLQGLLRPLF KNTSVGPLYS GCRLTLLRPE KDGEATGVDA   13860
```

```
ICTHRPDPTG  PGLDREQLYL  ELSQLTHSIT  ELGPYTLDRD  SLYVNGFTHR  SSVPTTSTGV    13920
VSEEPFTLNF  TINNLRYMAD  MGQPGSLKFN  ITDNVMQHLL  SPLFQRSSLG  ARYTGCRVIA    13980
LRSVKNGAET  RVDLLCTYLQ  PLSGPGLPIK  QVFHELSQQT  HGITRLGPYS  LDKDSLYLNG    14040
YNEPGPDEPP  TTPKPATTFL  PPLSEATTAM  GYHLKTLTLN  FTISNLQYSP  DMGKGSATFN    14100
STEGVLQHLL  RPLFQKSSMG  PFYLGCQLIS  LRPEKDGAAT  GVDTTCTYHP  DPVGPGLDIQ    14160
QLYWELSQLT  HGVTQLGFYV  LDRDSLFING  YAPQNLSIRG  EYQINFHIVN  WNLSNPDPTS    14220
SEYITLLRDI  QDKVTTLYKG  SQLHDTFRFC  LVTNLTMDSV  LVTVKALFSS  NLDPSLVEQV    14280
FLDKTLNASF  HWLGSTYQLV  DIHVTEMESS  VYQPTSSSST  QHFYLNFTIT  NLPYSQDKAQ    14340
PGTTNYQRNK  RNIEDALNQL  FRNSSIKSYF  SDCQVSTFRS  VPNRHHTGVD  SLCNFSPLAR    14400
RVDRVAIYEE  FLRMTRNGTQ  LQNFTLDRSS  VLVDGYSPNR  NEPLTGNSDL  P             14451

SEQ ID NO: 3            moltype = AA  length = 400
FEATURE                 Location/Qualifiers
source                  1..400
                        mol_type = protein
                        organism = Homo sapiens
SEQUENCE: 3
MTSYSYRQSS  ATSSFGGLGG  GSVRFGPGVA  FRAPSIHGGS  GGRGVSVSSA  RFVSSSSSGA    60
YGGGYGGVLT  ASDGLLAGNE  KLTMQNLNDR  LASYLDKVRA  LEAANGELEV  KIRDWYQKQG    120
PGPSRDYSHY  YTTIQDLRDK  ILGATIENSR  IVLQIDNARL  AADDFRTKFE  TEQALRMSVE    180
ADINGLRRVL  DELTLARTDL  EMQIEGLKEE  LAYLKKNHEE  EISTLRGQVG  GQVSEVEDSA    240
PGTDLAKILS  DMRSQYEVMA  EQNRKDAEAW  FTSRTEELNR  EVAGHTEQLQ  MSRSEVTDLR    300
RTLQGLEIEL  QSQLSMKAAL  EDTLAETEAR  FGAQLAHIQA  LISGIEAQLG  DVRADSERQN    360
QEYQRLMDIK  SRLEQEIATY  RSLLEGQEDH  YNNLSASKVL                            400

SEQ ID NO: 4            moltype = AA  length = 381
FEATURE                 Location/Qualifiers
source                  1..381
                        mol_type = protein
                        organism = Homo sapiens
SEQUENCE: 4
MAESHLLQWL  LLLLPTLCGP  GTAAWTTSSL  ACAQGPEFWC  QSLEQALQCR  ALGHCLQEVW    60
GHVGADDLCQ  ECEDIVHILN  KMAKEAIFQD  TMRKFLEQEC  NVLPLKLLMP  QCNQVLDDYF    120
PLVIDYFQNQ  TDSNGICMHL  GLCKSRQPEP  EQEPGMSDPL  PKPLRDPLPD  PLLDKLVLPV    180
LPGALQARPG  PHTQDLSEQQ  FPIPLPYCWL  CRALIKRIQA  MIPKGALAVA  VAQVCRVVPL    240
VAGGICQCLA  ERYSVILLDT  LLGRMLPQLV  CRLVLRCSMD  DSAGPRSPTG  EWLPRDSECH    300
LCMSVTTQAG  NSSEQAIPQA  MLQACVGSWL  DREKCKQFVE  QHTPQLLTLV  PRGWDAHTTC    360
QALGVCGTMS  SPLQCIHSPD  L                                                381
```

METHODS FOR THE DETECTION AND TREATMENT OF LUNG CANCER

CROSS REFERENCE TO RELATED APPLICATIONS

This application is a divisional of U.S. patent application Ser. No. 16/484,177, filed Aug. 7, 2019, which is a national stage entry under 35 U.S.C. § 371 of International Application No. PCT/US2018/017704, filed Feb. 9, 2018, which claims the benefit of priority of U.S. Provisional Application No. 62/456,731, filed Feb. 9, 2017, the disclosure of each of which is hereby incorporated by reference in its entirety

STATEMENT REGARDING FEDERALLY SPONSORED RESEARCH OR DEVELOPMENT

This invention was made with government support under grant number W81XWH-10-1-0632 awarded by the U.S. Department of the Army. The government has certain rights in the invention.

INCORPORATION OF SEQUENCE LISTING

The sequence listing that is contained in the file named "MDA0025-505TD1-US," which is 19.9 kilobytes as measured in Microsoft Windows operating system and was created on Mar. 28, 2023, is filed electronically herewith and incorporated herein by reference.

BACKGROUND

Lung cancer is the most prevalent cancer in the United States, with a five-year survival rate of less than 15%. Therapy for lung cancer is transitioning from use of a limited selection of therapies consisting of radiation, folate metabolism, platinum-based drugs, and/or taxol-based drugs to more targeted treatments that require histological characterization of the tumor and/or the presence or absence of key biomarker or therapeutic target proteins.

Lung cancer is the leading cancer killer world-wide and accounts for one in four of all cancer deaths in the U.S. Data from the National Lung Screening Trial (NLST) suggest that yearly screening with thoracic LDCT for high-risk current and ex-smokers reduces lung cancer mortality by 20% and total mortality by 7%. As a result, the U.S. Preventive Services Task Force (USPSTF) has recommended LDCT-screening for lung cancer in ever-smokers aged 55-80 years who have smoked 30 pack-years with no more than 15 years since quitting. However, the NLST study highlighted several important negative aspects associated with CT screening in terms of morbidity associated with over-diagnosis, treatment of benign nodules, and financial costs. Importantly, based on current screening criteria, the number of lives that would be saved through screening as a percentage of total number of deaths due to lung cancer is estimated to be relatively modest. Further, data from over a million subjects recruited from a general population cohort (UK Biobank and the European Prospective Investigation into Cancer and Nutrition (EPIC) study) indicate that less than 50% of incident lung cancer cases would have been eligible for screening based on the USPSTF criteria.

There is an abundance of literature on lung cancer risk prediction that provides convincing arguments on the benefit of replacing the dichotomous USPSTF screening criteria with a risk-based model when identifying subjects for CT-screening. For instance, recently it was estimated that 20% additional lung cancer deaths could be avoided by using a screening criterion based on individual risk-assessment. Considering that the information required to utilize such a risk-prediction tool can be readily ascertained by a general practitioner—or even self-assessed using an online risk-calculator—future lung cancer screening programs would seem likely to implement such tools when assessing screening eligibility.

An alternative to the USPSTF screening criteria would be an individual-level risk-based screening criteria that accurately estimates the risk of lung cancer within the near future (e.g., 1-3 years) for each individual. Several risk prediction models that rely on demographic data (age and sex) and risk factor data from questionnaires (primarily cigarette smoking) have been published. However, substantial improvement would be gained by incorporating biomarkers that incorporate information that cannot be captured with questionnaires.

Efforts to develop blood-based biomarkers for early detection of lung cancer are currently ongoing using a variety of analytical platforms that target nucleic acids, proteins, and metabolites, as well as circulating tumor cells and microparticles. For example, proteomic studies have led to the identification of several candidate circulating markers, including surfactant protein B (SFTPB), and its precursor form (Pro-SFTPB) that has been demonstrated to substantially improve lung cancer risk prediction in combination with smoking information when assayed using blood samples collected at the time of LDCT (AUC improvement: 0.67 to 0.74), as well as in pre-diagnostic blood samples from the Physicians Health Study. Other circulating proteins have been found to exhibit increased levels in lung cancer but with limited sensitivity and specificity to have utility as single markers for lung cancer screening.

Given the performance of SFTPB and its precursor form Pro-SFTPB in samples collected before the diagnosis of lung cancer, and in a screening setting, the potential of improving upon the USPSTF criteria using a panel of selected tumor-related proteins was investigated. The study was based on a high risk lung cancer prospective cohort, the Beta-Carotene and Retinol Efficacy Trial (CARET) study for building the panel, and cases and controls selected from two, large, general-population cohorts, the European Prospective Investigation into Cancer and Nutrition (EPIC) study, and the Northern Sweden Health and Disease Study (NSHDS) that involved 367,000 participants for validation.

SUMMARY

The present disclosure provides methods and kits for the early detection of lung cancer. The methods and kits use multiple assays of biomarkers contained within a biological sample obtained from a subject. The combined analysis of at least four biomarkers: CEA, CA125, CYFRA21-1, and Pro-SFTPB, provides high-accuracy diagnosis of lung cancer when screened against cohorts with known lung cancer status, i.e., lung cancer-positive, or lung cancer-negative. Optionally, the level of diacetylspermine (DAS) may be analyzed as well.

A regression model was identified that can predict the lung cancer status for a subject based on the levels of CEA, CA125, CYFRA21-1, and Pro-SFTPB that are found in a biological sample from the subject.

A biomarker-score based on four separate biomarkers was developed in a U.S. cohort, and external validation in two European cohorts confirmed that incorporating the biomarker-score with smoking information in an integrated risk prediction model provided a notable improvement in overall discrimination between cases and controls compared with a model based on smoking information alone. The integrated risk-prediction model identified 76% of future lung cancer cases in the validation sample, as compared to 42% of the USPSTF screening criteria, without increasing the number of false positives.

Accordingly, provided herein are:
methods of detection of lung cancer and risk of lung cancer in a subject;
methods of determining and/or quantifying the increased risk for the presence of lung cancer in a subject;
methods of determining the risk of a subject for harboring lung cancer;
each comprising measuring the level of CEA, CA125, CYFRA21-1, and Pro-SFTPB, and optionally, diacetylspermine (DAS), in a sample from the subject.

Also provided are methods of treatment or prevention of progression of lung cancer in a subject in whom the levels of CEA, CA125, CYFRA21-1, and pro-SFTPB, and optionally, diacetylspermine (DAS), classifies the subject as having or being at risk of harboring lung cancer.

Also provided are corresponding kits for determining the presence of indicators of lung cancer in a sample from the subject, for detection of lung cancer and risk of lung cancer in a subject, and for determining and/or quantifying the increased risk for the presence of lung cancer in a subject, comprising materials for measuring CEA, CA125, CYFRA21-1, and pro-SFTPB, and optionally, diacetylspermine (DAS) in the sample.

In some embodiments, biomarkers are measured in blood samples drawn from subjects. In some embodiments, the presence or absence of biomarkers in a biological sample can be determined. In some embodiments, the level of biomarkers in a biological sample can be quantified.

In some embodiments, a surface is provided to analyze a biological sample. In some embodiment, biomarkers of interest adsorb nonspecifically onto this surface. In some embodiments, receptors specific for biomarkers of interest are incorporated onto this surface. In some embodiments, the surface is associated with a particle, for example, a bead.

In some embodiments, the biomarker binds to a particular receptor molecule, and the presence or absence of the biomarker-receptor complex can be determined. In some embodiments, the amount of biomarker-receptor complex can be quantified. In some embodiments, the receptor molecule is linked to an enzyme to facilitate detection and quantification.

In some embodiments, the biomarker binds to a particular relay molecule, and the biomarker-relay molecule complex in turn binds to a receptor molecule. In some embodiments, the presence or absence of the biomarker-relay-receptor complex can be determined. In some embodiments, the amount of biomarker-relay-receptor complex can be quantified. In some embodiments, the receptor molecule is linked to an enzyme to facilitate detection and quantification.

In some embodiments, a biological sample is analyzed sequentially for individual biomarkers. In some embodiments, a biological sample is divided into separate portions to allow for simultaneous analysis for multiple biomarkers. In some embodiments, a biological sample is analyzed in a single process for multiple biomarkers.

In some embodiments, the absence or presence of biomarker can be determined by visual inspection. In some embodiments, the quantity of biomarker can be determined by use of a spectroscopic technique. In some embodiments, the spectroscopic technique is mass spectrometry. In some embodiments, the spectroscopic technique is UV/Vis spectrometry. In some embodiments, the spectroscopic technique is an excitation/emission technique such as fluorescence spectrometry.

In some embodiments, the analysis of biomarkers CEA, CA125, CYFRA21-1, and Pro-SFTPB can be combined with analysis of additional biomarkers. In some embodiments, the additional biomarkers can be protein biomarkers. In some embodiments, the additional biomarkers can be non-protein biomarkers. In some embodiments, the non-protein biomarkers can be circulating tumor DNA (ctDNA). In some embodiments, such a method may further comprise measuring the level of a metabolite, for example diacetylspermine (DAS), in the biological sample; wherein the amount of diacetylspermine (DAS) classifies the subject as being at risk of harboring lung cancer or not at risk of harboring lung cancer. In some embodiments, additional metabolites may be incorporated as necessary.

In some embodiments, a kit is provided for analysis of a biological sample. In some embodiments, the kit can contain the chemicals and reagents required to perform the analysis. In some embodiments, the kit contains a means for manipulating biological samples in order to minimize the required operator intervention. In some embodiments, the kit can record the outcome of an analysis digitally. In some embodiments, the kit can perform any needed mathematical processing of data generated by the analysis.

In another aspect, the disclosure provides a method of determining the risk of a subject for harboring lung cancer, comprising obtaining a biological sample from the subject; measuring the level of diacetylspermine (DAS) in the biological sample; wherein the amount of diacetylspermine (DAS) classifies the subject as being at risk of harboring lung cancer or not at risk of harboring lung cancer.

In another aspect, the disclosure provides a method of determining the risk of a subject for harboring lung cancer, comprising a plasma-derived biomarker panel and a protein marker panel wherein the plasma-derived biomarker panel comprises diacetylspermine (DAS); wherein the protein biomarker panel comprises CEA, CA125, CYFRA21-1, and pro-SFTPB; wherein the method comprises obtaining a biological sample from the subject; measuring the levels of the plasma-derived biomarkers and the protein biomarkers in the biological sample; wherein the amount of the plasma-derived biomarkers and the protein biomarkers classifies the subject as being at risk of harboring lung cancer or not at risk of harboring lung cancer.

In another aspect, the disclosure provides a method of determining the risk of a subject for harboring lung cancer, comprising determining the levels of one or more protein biomarkers and one or more metabolite markers, said method comprising obtaining a biological sample from the subject; contacting the sample with a first reporter molecule that binds CEA antigen; contacting the sample with a second reporter molecule that binds CA125 antigen; contacting the sample with a third reporter molecule that binds CYFRA21-1 antigen; and contacting the sample with a fourth reporter molecule that binds pro-SFTPB antigen; and determining the levels of the one or more biomarkers, wherein the one or more biomarkers is selected from the group consisting of diacetylspermine (DAS); wherein the amount of the first reporter molecule, the second reporter molecule, the third reporter molecule, the fourth reporter molecule, and the one or more biomarkers classifies the subject as being at risk of harboring lung cancer or not at risk of harboring lung cancer.

In another aspect, the disclosure provides a method of determining the risk of a subject for harboring lung cancer, comprising obtaining a biological sample from the subject; measuring the levels of CEA, CA125, CYFRA21-1, and pro-SFTPB antigens in the biological sample; and measuring the levels of one or more metabolite markers selected from the group consisting of diacetylspermine (DAS) in the biological sample; assigning the condition of the subject as either at risk of harboring lung cancer or not at risk of harboring lung cancer, as determined by statistical analysis of the levels of CEA antigen, CA125 antigen, CYFRA21-1 antigen, pro-SFTPB antigen, and diacetylspermine (DAS) in the biological sample.

In another aspect, the disclosure provides a method of treating a subject suspected of having or at risk of harboring lung cancer, comprising analyzing the subject for risk of harboring lung cancer with a method as described herein; administering a therapeutically effective amount of a treatment for the cancer. In one embodiment, the treatment is surgery, chemotherapy, immunotherapy, radiation therapy, targeted therapy, or a combination thereof. In another embodiment, such a method comprises at least one receptor molecule that selectively binds to an antigen selected from the group consisting of CEA, CA125, CYFRA21-1, and pro-SFTPB. In another embodiment, detection of the amount of CEA, CA125, CYFRA21-1, pro-SFTPB, and diacetylspermine (DAS) comprises the use of a solid particle. In another embodiment, the solid particle is a bead. In another embodiment, at least one of the reporter molecules is linked to an enzyme. In another embodiment, at least one of the protein or metabolite markers generates a detectable signal. In another embodiment, the detectable signal is detectable by a spectrometric method. In another embodiment, the spectrometric method is mass spectrometry. In another embodiment, such a method may comprise inclusion of patient history information into the assignment of having lung cancer or not having lung cancer. In another embodiment, such a method may comprise administering at least one alternate diagnostic test for a patient assigned as having lung cancer. In another embodiment, the at least one alternate diagnostic test comprises an assay or sequencing of at least one ctDNA.

In another aspect, the disclosure provides a kit for a method as described herein, comprising a reagent solution that comprises a first solute for detection of CEA antigen; a second solute for detection of CA125 antigen; a third solute for detection of CYFRA21-1 antigen; a fourth solute for detection of pro-SFTPB antigen; and a fifth solute for detection of diacetylspermine (DAS).

In another aspect, the disclosure provides a kit for a method as described herein, comprising a first reagent solution that comprises a first solute for detection of CEA antigen; a second reagent solution that comprises a second solute for detection of CA125 antigen; a third reagent solution that comprises a third solute for detection of CYFRA21-1 antigen; a fourth reagent solution that comprises a fourth solute for detection of pro-SFTPB; a fifth reagent solution that comprises a fifth solute for detection of diacetylspermine (DAS).

In one embodiment, such a kit comprises a device for contacting the reagent solutions with a biological sample. In another embodiment, such a kit comprises at least one surface with means for binding at least one antigen. In another embodiment, the at least one antigen is selected from the group consisting of CEA, CA125, CYFRA21-1, pro-SFTPB. In another embodiment, the at least one surface comprises a means for binding ctDNA.

In another aspect, the disclosure provides a method of treating a subject suspected of risk of harboring lung cancer, comprising: analyzing the subject for risk of harboring lung cancer with a method as described herein; administering a therapeutically effective amount of a treatment for the lung cancer. In one embodiment, the treatment is surgery, chemotherapy, radiation therapy, targeted therapy, or a combination thereof. In another embodiment, such a method comprises at least one receptor molecule that selectively binds to an antigen selected from the group consisting of CEA, CA125, CYFRA21-1, and pro-SFTPB. In another embodiment, detection of the amount of CEA, CA125, CYFRA21-1, pro-SFTPB, or diacetylspermine (DAS) comprises the use of a solid particle. In another embodiment, the solid particle is a bead. In another embodiment, at least one of the reporter molecules is linked to an enzyme. In another embodiment, at least one of the protein or metabolite markers generates a detectable signal. In another embodiment, the detectable signal is detectable by a spectrometric method. In another embodiment, the spectrometric method is mass spectrometry. In another embodiment, such a method comprises inclusion of patient history information into the assignment of having lung cancer or not having lung cancer. In another embodiment, such a method comprises administering at least one alternate diagnostic test for a patient assigned as having lung cancer. In another embodiment, the at least one alternate diagnostic test comprises an assay or sequencing of at least one ctDNA.

In another aspect, the disclosure provides a method of treatment or prevention of progression of lung cancer in a subject in whom the levels of CEA antigen, CA125 antigen, CYFRA21-1 antigen, and pro-SFTPB antigen classifies the subject as having or being at risk of harboring lung cancer comprising one or more of administering a chemotherapeutic drug to the subject with lung cancer; administering therapeutic radiation to the subject with lung cancer; and surgery for partial or complete surgical removal of cancerous tissue in the subject with lung cancer. In one embodiment, the levels of CEA antigen, CA125 antigen, CYFRA21-1 antigen, and pro-SFTPB antigen are elevated. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that does not have lung cancer. In another embodiment, the reference subject or group is healthy. In another embodiment, the AUC (95% CI) is at least 0.83, or is at least 0.80. In another embodiment, the classification of the subject as having lung cancer has a sensitivity of 0.76 and 0.42 at 78% and 94% specificity, respectively. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has adenocarcinoma. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has squamous cell cancer. In another embodiment, the AUC (95% CI) is at least 0.830 or at least 0.800. In another embodiment, the classification of the subject as having lung cancer has a sensitivity of 0.76 and 0.42 at 78% and 94% specificity, respectively. In another embodiment, the lung cancer is diagnosed at or before the borderline resectable stage. In another embodiment, the lung cancer is diagnosed at the resectable stage.

In another aspect, the disclosure provides a method of treatment or prevention of progression of lung cancer in a subject in whom the levels of CEA antigen, CA125 antigen, CYFRA21-1 antigen, pro-SFTPB antigen, diacetylspermine (DAS) classifies the subject as having or being at risk of harboring lung cancer comprising one or more of administering a chemotherapeutic drug to the subject with lung cancer; administering therapeutic radiation to the subject with lung cancer; and surgery for partial or complete surgical removal of cancerous tissue in the subject with lung cancer. In one embodiment, the levels of CEA antigen, CA125 antigen, CYFRA21-1 antigen, and pro-SFTPB antigen are elevated. In another embodiment, the levels of CEA antigen, CA125 antigen, CYFRA21-1 antigen, pro-SFTPB antigen are elevated in comparison to the levels of CEA antigen, CA125 antigen, CYFRA21-1 antigen, pro-SFTPB antigen in a reference subject or group that does not have lung cancer. In another embodiment, the reference subject or group is healthy. In another embodiment, the levels of CEA antigen, CA125 antigen, CYFRA21-1 antigen, pro-SFTPB antigen are elevated in comparison to the levels of CEA antigen, CA125 antigen, CYFRA21-1 antigen, pro-SFTPB antigen in a reference subject or group that has adenocarcinoma. In another embodiment, the levels of CEA antigen, CA125 antigen, CYFRA21-1 antigen, pro-SFTPB antigen are elevated in comparison to the levels of CEA antigen, CA125 antigen, CYFRA21-1 antigen, pro-SFTPB antigen in a reference subject or group that has squamous cell cancer. In another embodiment, the subject is at high-risk of lung cancer.

In another aspect, the disclosure provides a method of treating a subject suspected of risk of harboring lung cancer, comprising analyzing the subject for risk of harboring lung cancer with a method as disclosed herein; administering a therapeutically effective amount of a treatment for the lung cancer. In one embodiment, the treatment is surgery, chemotherapy, radiation therapy, targeted therapy, or a combination thereof.

DETAILED DESCRIPTION

Figure 1:
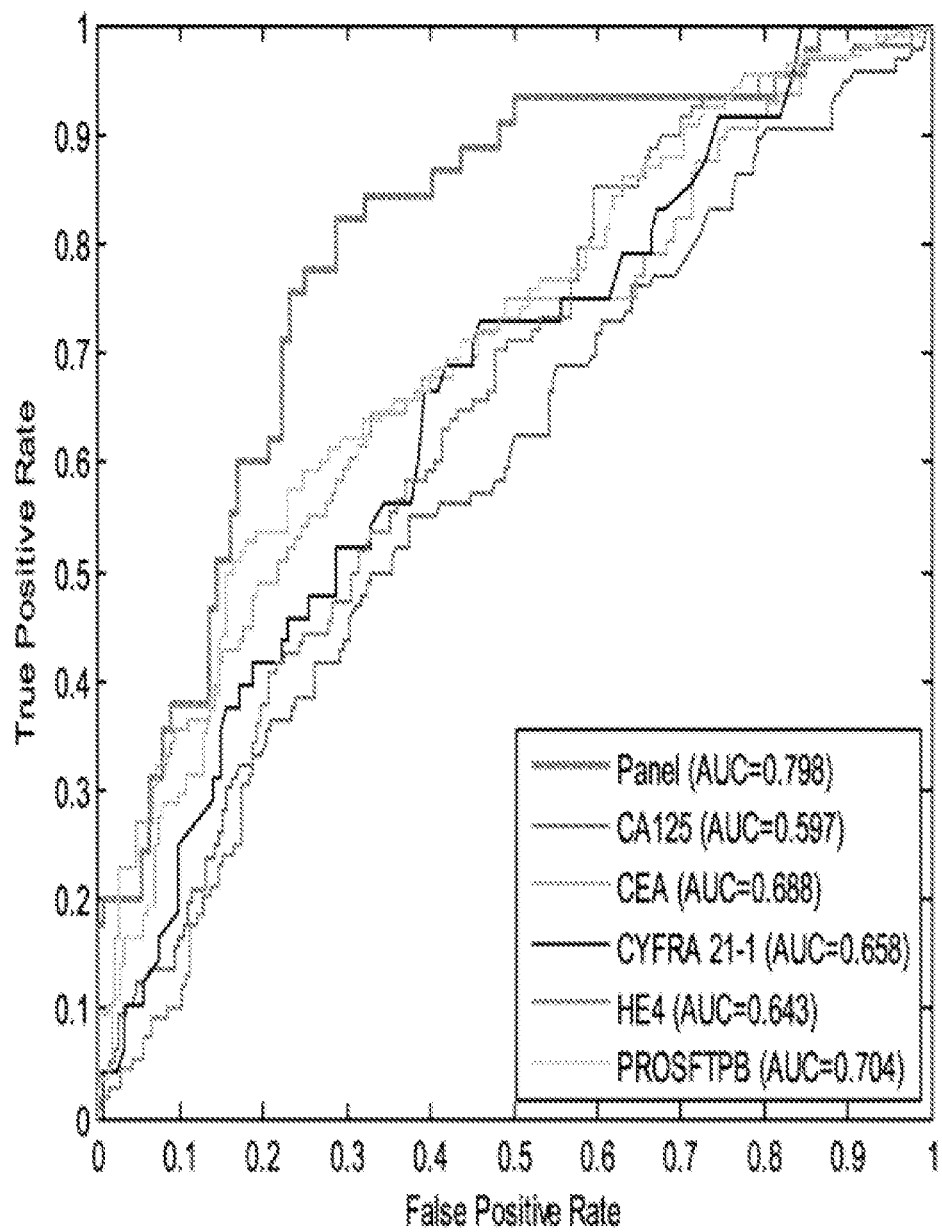
FIG. 1 depicts ROC curves for all 5 biomarkers in CARET along with the 4 marker panel.

In one aspect, the invention provides a method of determining the risk of a subject for harboring lung cancer, comprising obtaining a biological sample from the subject; measuring the level of CEA in the biological sample; measuring the level of CA125 in the biological sample; measuring the level of CYFRA21-1 in the biological sample; measuring the level of Pro-SFTPB in the biological sample; wherein the amount of CEA, CA125, CYFRA21-1, and Pro-SFTPB classifies the subject as being at risk of harboring lung cancer or not at risk of harboring lung cancer.

In another aspect, the invention provides a method of determining the risk of a subject for harboring lung cancer, comprising obtaining a biological sample from the subject; contacting the sample with a first reporter molecule that binds CEA; contacting the sample with a second reporter molecule that binds CA125; contacting the sample with a third reporter molecule that binds CYFRA21-1; contacting the sample with a fourth reporter molecule that binds Pro-SFTPB; wherein the amount of the first reporter molecule, the second reporter molecule, the third reporter molecule, and the fourth reporter molecule classifies the subject as being at risk of harboring lung cancer or not at risk of harboring lung cancer.

In another aspect, the invention provides a method of determining the risk of a subject for harboring lung cancer, comprising obtaining a biological sample from the subject; providing a surface that binds CEA, CA125, CYFRA21-1, and Pro-SFTPB; incubating the surface with the biological sample; contacting the surface with a first reporter molecule that binds CEA; contacting the surface with a second reporter molecule that binds CA125; contacting the surface with a third reporter molecule that binds CYFRA21-1; contacting the surface with a fourth reporter molecule that binds Pro-SFTPB; measuring the amount of the first reporter molecule that is associated with the surface; measuring the amount of the second reporter molecule that is associated with the surface; measuring the amount of the third reporter molecule that is associated with the surface; measuring the amount of the fourth reporter molecule that is associated with the surface; wherein the amount of the first reporter molecule, the second reporter molecule, the third reporter molecule, and the fourth reporter molecule classifies the subject as being at risk of harboring lung cancer or not at risk of harboring lung cancer.

In another aspect, the invention provides a method of determining the risk of a subject for harboring lung cancer, comprising obtaining a biological sample from the subject; providing a first surface with means for binding CEA; providing a second surface with means for binding CA125; providing a third surface with means for binding CYFRA21-1; providing a fourth surface with means for binding Pro-SFTPB; incubating the first surface with the biological sample; incubating the second surface with the biological sample; incubating the third surface with the biological sample; incubating the fourth surface with the biological sample; contacting the first surface with a first reporter molecule that binds CEA; contacting the second surface with a second reporter molecule that binds CA125; contacting the third surface with a third reporter molecule that binds CYFRA21-1; contacting the fourth surface with a third reporter molecule that binds pro-SFTPB; measuring the amount of the first reporter molecule associated with the first surface; measuring the amount of the second reporter molecule associated with the second surface; measuring the amount of the third reporter molecule associated with the third surface; measuring the amount of the third reporter molecule associated with the fourth surface; wherein the amount of the first reporter molecule, the second reporter molecule, the third reporter molecule, and the fourth reporter molecule classifies the subject as being at risk of harboring lung cancer or not at risk of harboring lung cancer.

A method of determining the risk of a subject for harboring lung cancer, comprising obtaining a biological sample from the subject; providing a surface with means for binding CEA, CA125, CYFRA21-1, and Pro-SFTPB; incubating the surface with the biological sample; contacting the surface with a first relay molecule that binds CEA; contacting the surface with a second relay molecule that binds CA125; contacting the surface with a third relay molecule that binds CYFRA21-1; contacting the surface with a fourth relay molecule that binds Pro-SFTPB; contacting the surface with a first reporter molecule that binds to the first relay molecule; contacting the surface with a second reporter molecule that binds to the second relay molecule; contacting the surface with a third reporter molecule that binds to the third relay molecule; contacting the surface with a fourth reporter molecule that binds to the fourth relay molecule; measuring the amount of the first reporter molecule associated with the first relay molecule and CEA; measuring the amount of the second reporter molecule associated with the second relay molecule and CA125; measuring the amount of the third reporter molecule associated with the third relay molecule and CYFRA21-1; measuring the amount of the fourth reporter molecule associated with the fourth relay molecule and Pro-SFTPB; wherein the amount of the first reporter molecule, the second reporter molecule, the third reporter molecule, and the fourth reporter molecule classifies the subject as being at risk of harboring lung cancer or not at risk of harboring lung cancer.

In another aspect, the invention provides a method of determining the risk of a subject for harboring lung cancer, comprising obtaining a biological sample from the subject; providing a first surface with means for binding CEA; providing a second surface with means for binding CA125; providing a third surface with means for binding CYFRA21-1; providing a fourth surface with means for binding Pro-SFTPB; incubating the first surface with the biological sample; incubating the second surface with the biological sample; incubating the third surface with the biological sample; incubating the fourth surface with the biological sample; contacting the first surface with a first relay molecule that binds CEA; contacting the second surface with a second relay molecule that binds CA125; contacting the third surface with a third relay molecule that binds CYFRA21-1; contacting the fourth surface with a fourth relay molecule that binds Pro-SFTPB; contacting the first surface with a first reporter molecule that binds to the first relay molecule; contacting the second surface with a second reporter molecule that binds to the second relay molecule; contacting the third surface with a third reporter molecule that binds to the third relay molecule; contacting the fourth surface with a fourth reporter molecule that binds to the fourth relay molecule; measuring the amount of the first reporter molecule that is associated with the first relay molecule and CEA; measuring the amount of the second reporter molecule that is associated with the second relay molecule and CA125; measuring the amount of the third reporter molecule that is associated with the third relay molecule and CYFRA21-1; measuring the amount of the fourth reporter molecule that is associated with the fourth relay molecule and Pro-SFTPB; wherein the amount of the first reporter molecule, the second reporter molecule, the third reporter molecule, and the fourth reporter molecule classifies the subject as being at risk of harboring lung cancer or not at risk of harboring lung cancer.

In one embodiment, the amounts of CEA, CA125, CYFRA21-1, and pro-SFTPB or the reporter molecules bound thereto are elevated in the subject relative to a healthy subject. In other embodiments, at least one of the surfaces further comprises at least one receptor molecule that selectively binds to a biomarker selected from CEA, CA125, CYFRA21-1, and Pro-SFTPB. In another embodiment, the amounts of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that does not have lung cancer. In another embodiment, at least one of the surfaces further comprises at least one receptor molecule that selectively binds to a biomarker or antigen selected from CEA, CA125, CYFRA21-1, and Pro-SFTPB. In another embodiment, the reference subject or group is healthy. In another embodiment, such methods further comprising: measuring the level of diacetylspermine (DAS) in the biological sample; wherein the amount of diacetylspermine (DAS) classifies the patient as being at risk of harboring lung cancer or not at risk of harboring lung cancer. In another embodiment, the sample comprises a biological sample selected from blood, plasma, and serum. In another embodiment, the biological sample is serum. In another embodiment, the amount of CEA, CA125, CYFRA21-1, and pro-SFTPB is quantified. In another embodiment, the concentrations of CEA, CA125, CYFRA21-1, Pro-SFTPB, and diacetylspermine (DAS) are measured. In another embodiment, the subject is determined to have lung cancer based on the measured concentrations of the biomarkers. In another embodiment, the measured concentrations are used to calculate a biomarker score based on sensitivity and specificity values at a cutoff set forth in Table 10. In another embodiment, such methods further comprising the steps of: comparing the measured concentrations of each biomarker in the biological sample to the prediction of a statistical model. In another embodiment, the panel is selected from the group consisting of: a. the panel consisting of CEA, CA125, CYFRA21-1, and Pro-SFTPB; or b. the panel consisting of CEA, CA125, CYFRA21-1, Pro-SFTPB, and diacetylspermine (DAS). In another embodiment, at least one of the surfaces is the surface of a solid particle. In another embodiment, the solid particle is a bead. In another embodiment, at least one of the reporter molecules is linked to an enzyme. In another embodiment, at least one of the reporter molecules provides a detectable signal. In another embodiment, the detectable signal is detectable by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the spectrometric method is mass spectrometry. In another embodiment, the panel comprises biomarkers that have been identified by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the panel comprises biomarkers that have been identified by UV-visible spectroscopy or proton NMR spectroscopy. In another embodiment, the first reporter binds selectively to CEA. In another embodiment, the second reporter binds selectively to CA125. In another embodiment, the third reporter binds selectively to CYFRA21-1. In another embodiment, the fourth reporter binds selectively to Pro-SFTPB. In another embodiment, determination of CEA, CA125, CYFRA21-1, and pro-SFTPB levels is made at substantially the same time. In another embodiment, determination of CEA, CA125, CYFRA21-1, and pro-SFTPB levels is made in a stepwise manner. In another embodiment, such methods comprise inclusion of subject history information into the assignment of having lung cancer or not having lung cancer. In another embodiment, such methods comprise administering at least one alternate diagnostic test for a subject assigned as having lung cancer. In another embodiment, the at least one alternate diagnostic test comprises an assay or sequencing of at least one ctDNA.

In another aspect, the invention provides a method of treating a subject suspected of harboring lung cancer, comprising analyzing the subject for risk of harboring lung cancer with a method as described herein, and administering a therapeutically effective amount of a treatment for the cancer. In one embodiment, the treatment is surgery, chemotherapy, immunotherapy, radiation therapy, targeted therapy, or a combination thereof. In another embodiment, the classification of the subject as having lung cancer has a sensitivity of 0.76 and 0.42 at 78% and 94% specificity, respectively. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has adenocarcinoma. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has squamous cell cancer. In another embodiment, such methods further comprise comparing the amount of CEA, CA125, CYFRA21-1, and pro-SFTPB with a cutoff value as exemplified in Table 10. In another embodiment, the cutoff value comprises an AUC (95% CI) of at least 0.83. In another embodiment, the cutoff value comprises an AUC (95% CI) of at least 0.80. In another embodiment, the classification of the subject as having lung cancer has a sensitivity of 0.76 and 0.42 at 78% and 94% specificity, respectively. In another embodiment, the lung cancer is diagnosed at or before the borderline resectable stage. In another embodiment, the lung cancer is diagnosed at the resectable stage.

In another aspect, the invention provides a method of determining the risk of a subject for harboring lung cancer, comprising obtaining a biological sample from the subject; measuring the level of CEA in the biological sample by contacting the biological sample with a CEA antibody and observing binding between CEA and the antibody; measuring the level of CA125 in the biological sample by contacting the biological sample with a CA125 antibody and observing binding between CA125 and the antibody; measuring the level of CYFRA21-1 in the biological sample by contacting the biological sample with a CYFRA21-1 antibody and observing binding between CYFRA21-1 and the antibody; measuring the level of pro-SFTPB in the biological sample by contacting the biological sample with a pro-SFTPB antibody and observing binding between pro-SFTPB and the antibody; assigning the condition of the subject as either at risk of harboring lung cancer or not at risk of harboring lung cancer, as determined by the measurements of CEA, CA125, CYFRA21-1, and pro-SFTPB levels.

In another aspect, the invention provides a method of determining the risk of a subject for harboring lung cancer, comprising obtaining a biological sample from the subject; measuring the level of CEA in the biological sample; measuring the level of CA125 in the biological sample; measuring the level of CYFRA21-1 in the biological sample; measuring the level of pro-SFTPB in the biological sample; determining the level of CEA relative to a first standard value, wherein the ratio is predictive of presence of lung cancer; determining the level of CA125 relative to a second standard value, wherein the ratio is predictive of presence of lung cancer; determining the level of CYFRA21-1 relative to a third standard value, wherein the ratio is predictive of presence of lung cancer; and determining the level of pro-SFTPB relative to a fourth standard value, wherein the ratio is predictive of presence of lung cancer; and assigning the condition of the subject as either at risk of harboring lung cancer or not at risk of harboring lung cancer, as determined by statistical analysis of the ratios of CEA, CA125, CYFRA21-1, and pro-SFTPB levels.

In another aspect, the invention provides a method of predicting the risk of a subject for harboring lung, comprising obtaining a biological sample from the subject; measuring the levels of the CEA, CA125, CYFRA21-1, and pro-SFTPB biomarkers in the biological sample; and calculating a predictive factor as determined by statistical analysis of the CEA, CA125, CYFRA21-1, and pro-SFTPB levels.

In another aspect, the invention provides a method of determining the risk of a subject for harboring lung cancer, comprising obtaining a biological sample from the subject; measuring the levels of CEA, CA125, CYFRA21-1, and pro-SFTPB biomarkers in the biological sample; assigning the condition of the subject as either at risk of harboring lung cancer or not at risk of harboring lung cancer, as determined by statistical analysis of the levels of CEA, CA125, CYFRA21-1, and pro-SFTPB in the biological sample.

In another aspect, the invention provides a method for determining the risk of a subject for harboring lung cancer using a biological sample obtained from a subject suspected of having lung cancer, comprising assaying for the level of CEA present in the biological sample using at least one antibody or antibody fraction specific for CEA; and assaying for the level of CA125 present in the biological sample using at least one antibody or antibody fraction specific for CA125; and assaying for the level of CYFRA21-1 present in the biological sample using at least one antibody or antibody fraction specific for CYFRA21-1; and assaying for the level of pro-SFTPB present in the biological sample using at least one antibody or antibody fraction specific for pro-SFTPB; and determining whether the levels of CEA, CA125, CYFRA21-1, and pro-SFTPB are indicative of the subject having lung cancer.

In another aspect, the invention provides a method for determining the risk of a subject for harboring lung cancer comprising obtaining a biological sample from a subject; performing an immunoassay on the sample with an anti-CEA antibody or antigen-binding fragment thereof; performing an immunoassay on the sample with an anti-CA125 antibody or antigen-binding fragment thereof; performing an immunoassay on the sample with an anti-CYFRA21-1 antibody or antigen-binding fragment thereof; performing an immunoassay on the sample with an anti-pro-SFTPB antibody or antigen-binding fragment thereof; wherein binding of the antibodies is indicative of lung cancer in the subject and the immunoassay can detect early stage lung cancer.

In another aspect, the invention provides a method for determining the risk of a subject for harboring lung cancer comprising obtaining a biological sample from the subject; performing an immunoassay with an anti-CEA antibody or antigen-binding fragment thereof; performing an immunoassay with an anti-CA125 antibody or antigen-binding fragment thereof; performing an immunoassay with an anti-CYFRA21-1 antibody or antigen-binding fragment thereof; performing an immunoassay with an anti-pro-SFTPB antibody or antigen-binding fragment thereof; determining whether the levels of CEA, CA125, CYFRA21-1, and pro-SFTPB are indicative of the subject having lung cancer. In one embodiment, the levels of CEA, CA125, CYFRA21-1, and pro-SFTPB are elevated in the subject relative to a healthy subject. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that does not have lung cancer. In another embodiment, the reference subject or group is healthy. In another embodiment, at least one of the surfaces further comprises at least one receptor molecule that selectively binds to a biomarker or antigen selected from CEA, CA125, CYFRA21-1, and Pro-SFTPB. In another embodiment, at least one of the surfaces is the surface of a solid particle. In another embodiment, such methods further comprise measuring the level of diacetylspermine (DAS) in the biological sample; wherein the amount of diacetylspermine (DAS) classifies the patient as being at risk of harboring lung cancer or not at risk of harboring lung cancer. In another embodiment, the sample comprises a biological sample selected from blood, plasma, and serum. In another embodiment, the biological sample is serum. In another embodiment, the amount of CEA, CA125, CYFRA21-1, and pro-SFTPB is quantified. In another embodiment, detection of the amount of CEA, CA125, CYFRA21-1, pro-SFTPB, and diacetylspermine (DAS) comprises the use of a solid particle. In another embodiment, the solid particle is a bead. In another embodiment, at least one of the reporter molecules is linked to an enzyme. In another embodiment, at least one of the reporter molecules provides a detectable signal. In another embodiment, the detectable signal is detectable by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the concentrations of CEA, CA125, CYFRA21-1, Pro-SFTPB, and diacetylspermine (DAS) are measured. In another embodiment, the subject is determined to have lung cancer based on the measured concentrations of the biomarkers. In another embodiment, the measured concentrations are used to calculate a biomarker score based on sensitivity and specificity values at a cutoff set forth in Table 10. In another embodiment, such methods further comprise the steps of: comparing the measured concentrations of each biomarker in the biological sample to the prediction of a statistical model. In another embodiment, the panel is selected from the group consisting of: a. the panel consisting of CEA, CA125, CYFRA21-1, and Pro-SFTPB; or b. the panel consisting of CEA, CA125, CYFRA21-1, Pro-SFTPB, and diacetylspermine (DAS). In another embodiment, the panel comprises biomarkers that have been identified by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the panel comprises biomarkers that have been identified by UV-visible spectroscopy or proton NMR spectroscopy. In another embodiment, the first reporter binds selectively to CEA. In another embodiment, the second reporter binds selectively to CA125. In another embodiment, the third reporter binds selectively to CYFRA21-1. In another embodiment, the fourth reporter binds selectively to Pro-SFTPB. In another embodiment, determination of CEA, CA125, CYFRA21-1, and pro-SFTPB levels is made at substantially the same time. In another embodiment, determination of CEA, CA125, CYFRA21-1, and pro-SFTPB levels is made in a stepwise manner. In another embodiment, such methods further comprise inclusion of subject history information into the assignment of having lung cancer or not having lung cancer. In another embodiment, such methods comprise administering at least one alternate diagnostic test for a subject assigned as having lung cancer. In another embodiment, the at least one alternate diagnostic test comprises an assay or sequencing of at least one ctDNA.

In another aspect, the invention provides a method of treating a subject suspected of harboring lung cancer, comprising analyzing the subject for risk of harboring lung cancer with a method as described herein; and administering a therapeutically effective amount of a treatment for the cancer. In another embodiment, the treatment is surgery, chemotherapy, immunotherapy, radiation therapy, targeted therapy, or a combination thereof. In another embodiment, the classification of the subject as having lung cancer has a sensitivity of 0.76 and 0.42 at 78% and 94% specificity, respectively. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has adenocarcinoma. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has squamous cell cancer. In another embodiment, such methods further comprise comparing the amount of CEA, CA125, CYFRA21-1, and pro-SFTPB with a cutoff value as exemplified in Table 10. In another embodiment, the cutoff value comprises an AUC (95% CI) of at least 0.83. In another embodiment, the cutoff value comprises an AUC (95% CI) of at least 0.80. In another embodiment, the classification of the subject as having lung cancer has a sensitivity of 0.76 and 0.42 at 78% and 94% specificity, respectively. In another embodiment, the lung cancer is diagnosed at or before the borderline resectable stage. In another embodiment, the lung cancer is diagnosed at the resectable stage.

In another aspect, the invention provides a kit for the methods disclosed herein, comprising a reagent solution that comprises a first solute for detection of CEA; a second solute for detection of CA125; a third solute for detection of CYFRA21-1; and a fourth solute for detection of pro-SFTPB.

In another aspect, the invention provides a kit for the methods disclosed herein, comprising a first reagent solution that comprises a first solute for detection of CEA; a second reagent solution that comprises a second solute for detection of CA125; a third reagent solution that comprises a third solute for detection of CYFRA21-1; and a fourth reagent solution that comprises a fourth solute for detection of pro-SFTPB. In another embodiment, such methods further comprise: a reagent solution that comprises a first solute for detection of CEA antigen; a second solute for detection of CA125 antigen; a third solute for detection of CYFRA21-1 antigen; a fourth solute for detection of pro-SFTPB antigen; and a fifth solute for detection of diacetylspermine (DAS). In another embodiment, such methods further comprise a device for contacting the reagent solutions with a biological sample. In another embodiment, such methods comprise at least one surface with means for binding at least one biomarker or antigen. In another embodiment, the at least one biomarker is selected from the group consisting of CEA, CA125, CYFRA21-1, and pro-SFTPB. In another embodiment, the at least one surface comprises a means for binding ctDNA. In another embodiment, such methods further comprise an antibody or antigen-binding fragment thereof that binds to the metabolite biomarker diacetylspermine (DAS). In another embodiment, the antigen-binding reagent comprises antibodies or antigen-binding fragments thereof, RNA, DNA, or RNA/DNA hybrids.

In another aspect, the invention provides a method of determining the risk of a subject for harboring lung cancer, comprising obtaining a biological sample from the patient; measuring the level of diacetylspermine (DAS) in the biological sample; wherein the amount of diacetylspermine (DAS) classifies the subject as being at risk of harboring lung cancer or not at risk of harboring lung cancer.

In another aspect, the invention provides a method of determining the risk of a subject for harboring lung cancer, comprising a plasma-derived biomarker panel and a protein marker panel: wherein the plasma-derived biomarker panel comprises diacetylspermine (DAS); wherein the protein biomarker panel comprises CEA, CA125, CYFRA21-1, and pro-SFTPB; wherein the method comprises: obtaining a biological sample from the subject; measuring the levels of the plasma-derived biomarkers and the protein biomarkers in the biological sample; wherein the amount of the plasma-derived biomarkers and the protein biomarkers classifies the subject as being at risk of harboring lung cancer or not at risk of harboring lung cancer.

In another aspect, the invention provides a method of determining the risk of a subject for harboring lung cancer, comprising determining the levels of one or more protein biomarkers and one or more metabolite markers, said method comprising: obtaining a biological sample from the subject; contacting the sample with a first reporter molecule that binds CEA antigen; contacting the sample with a second reporter molecule that binds CA125 antigen; contacting the sample with a third reporter molecule that binds CYFRA21-1 antigen; and contacting the sample with a fourth reporter molecule that binds pro-SFTPB antigen; and determining the levels of the one or more biomarkers, wherein the one or more biomarkers is selected from the group consisting of diacetylspermine (DAS); wherein the amount of the first reporter molecule, the second reporter molecule, the third reporter molecule, the fourth reporter molecule, and the one or more biomarkers classifies the subject as being at risk of harboring lung cancer or not at risk of harboring lung cancer.

In another aspect, the invention provides a method of determining the risk of a subject for harboring lung cancer, comprising obtaining a biological sample from the subject; measuring the levels of CEA, CA125, CYFRA21-1, and pro-SFTPB antigens in the biological sample; and measuring the levels of one or more metabolite markers selected from the group consisting of diacetylspermine (DAS) in the biological sample; assigning the condition of the subject as either at risk of harboring lung cancer or not at risk of harboring lung cancer, as determined by statistical analysis of the levels of CEA antigen, CA125 antigen, CYFRA21-1 antigen, pro-SFTPB antigen, and diacetylspermine (DAS) in the biological sample. In one embodiment, the levels of CEA, CA125, CYFRA21-1, and pro-SFTPB or the reporter molecules bound thereto are elevated in the subject relative to a healthy subject. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that does not have lung cancer. In another embodiment, the reference subject or group is healthy. In another embodiment, such methods comprise at least one receptor molecule that selectively binds to a biomarker or antigen selected from the group consisting of CEA, CA125, CYFRA21-1, and pro-SFTPB. In another embodiment, such methods further comprise: measuring the level of diacetylspermine (DAS) in the biological sample; wherein the amount of diacetylspermine (DAS) classifies the patient as being at risk of harboring lung cancer or not at risk of harboring lung cancer. In another embodiment, the sample comprises a biological sample selected from blood, plasma, and serum. In another embodiment, the biological sample is serum. In another embodiment, the amount of CEA, CA125, CYFRA21-1, and pro-SFTPB is quantified. In another embodiment, detection of the amount of CEA, CA125, CYFRA21-1, pro-SFTPB, and diacetylspermine (DAS) comprises the use of a solid particle. In another embodiment, the solid particle is a bead. In another embodiment, at least one of the reporter molecules is linked to an enzyme. In another embodiment, at least one of the reporter molecules provides a detectable signal. In another embodiment, the detectable signal is detectable by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the concentrations of CEA, CA125, CYFRA21-1, Pro-SFTPB, and diacetylspermine (DAS) are measured. In another embodiment, the subject is determined to have lung cancer based on the measured concentrations of the biomarkers. In another embodiment, the measured concentrations are used to calculate a biomarker score based on sensitivity and specificity values at a cutoff set forth in Table 10. In another embodiment, such methods further comprise the steps of: comparing the measured concentrations of each biomarker in the biological sample to the prediction of a statistical model. In another embodiment, the panel is selected from the group consisting of: a. the panel consisting of CEA, CA125, CYFRA21-1, and Pro-SFTPB; or b. the panel consisting of CEA, CA125, CYFRA21-1, Pro-SFTPB, and diacetylspermine (DAS). In another embodiment, the panel comprises biomarkers that have been identified by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the panel comprises biomarkers that have been identified by UV-visible spectroscopy or proton NMR spectroscopy. In another embodiment, the first reporter binds selectively to CEA. In another embodiment, the second reporter binds selectively to CA125. In another embodiment, the third reporter binds selectively to CYFRA21-1. In another embodiment, the fourth reporter binds selectively to Pro-SFTPB. In another embodiment, determination of CEA, CA125, CYFRA21-1, and pro-SFTPB levels is made at substantially the same time. In another embodiment, determination of CEA, CA125, CYFRA21-1, and pro-SFTPB levels is made in a stepwise manner. In another embodiment, such methods further comprise inclusion of subject history information into the assignment of having lung cancer or not having lung cancer. In another embodiment, such methods comprise administering at least one alternate diagnostic test for a subject assigned as having lung cancer. In another embodiment, the at least one alternate diagnostic test comprises an assay or sequencing of at least one ctDNA.

In another aspect, the invention provides a method of treating a subject suspected of harboring lung cancer, comprising analyzing the subject for risk of harboring lung cancer with a method as recited herein; and administering a therapeutically effective amount of a treatment for the cancer. In another embodiment, the treatment is surgery, chemotherapy, immunotherapy, radiation therapy, targeted therapy, or a combination thereof. In another embodiment, the classification of the subject as having lung cancer has a sensitivity of 0.76 and 0.42 at 78% and 94% specificity, respectively. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has adenocarcinoma. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has squamous cell cancer. In another embodiment, such methods further comprise comparing the amount of CEA, CA125, CYFRA21-1, and pro-SFTPB with a cutoff value as exemplified in Table 10. In another embodiment, the cutoff value comprises an AUC (95% CI) of at least 0.83. In another embodiment, the cutoff value comprises an AUC (95% CI) of at least 0.80. In another embodiment, the classification of the subject as having lung cancer has a sensitivity of 0.76 and 0.42 at 78% and 94% specificity, respectively. In another embodiment, the lung cancer is diagnosed at or before the borderline resectable stage. In another embodiment, the lung cancer is diagnosed at the resectable stage.

In another embodiment, the invention provides a kit for the method as described herein, comprising: a reagent solution that comprises a first solute for detection of CEA antigen; a second solute for detection of CA125 antigen; a third solute for detection of CYFRA21-1 antigen; a fourth solute for detection of pro-SFTPB antigen; and a fifth solute for detection of diacetylspermine (DAS).

In another embodiment, the invention provides a kit for a method as described herein, comprising a first reagent solution that comprises a first solute for detection of CEA antigen; a second reagent solution that comprises a second solute for detection of CA125 antigen; a third reagent solution that comprises a third solute for detection of CYFRA21-1 antigen; a fourth reagent solution that comprises a fourth solute for detection of pro-SFTPB; a fifth reagent solution that comprises a fifth solute for detection of diacetylspermine (DAS). In another embodiment, such a kit further comprises: a reagent solution that comprises a first solute for detection of CEA antigen; a second solute for detection of CA125 antigen; a third solute for detection of CYFRA21-1 antigen; a fourth solute for detection of pro-SFTPB antigen; and a fifth solute for detection of diacetylspermine (DAS). In another embodiment, the kit comprises a device for contacting the reagent solutions with a biological sample. In another embodiment, such a kit comprises at least one surface with means for binding at least one biomarker or antigen. In another embodiment, the at least one biomarker is selected from the group consisting of CEA, CA125, CYFRA21-1, and pro-SFTPB. In another embodiment, the at least one surface comprises a means for binding ctDNA. In another embodiment, such a kit further comprises an antibody or antigen-binding fragment thereof that binds to the metabolite biomarker diacetylspermine (DAS). In another embodiment, the antigen-binding reagent comprises antibodies or antigen-binding fragments thereof, RNA, DNA, or RNA/DNA hybrids.

In another aspect, the invention provides a method of treatment or prevention of progression of lung cancer in a subject in whom the levels of CEA antigen, CA125 antigen, CYFRA21-1 antigen, and pro-SFTPB antigen classifies the subject as having or being at risk of harboring lung cancer comprising one or more of: administering a chemotherapeutic drug to the subject with lung cancer; administering therapeutic radiation to the subject with lung cancer; and surgery for partial or complete surgical removal of cancerous tissue in the subject with lung cancer.

In another aspect, the invention provides a method of treatment or prevention of progression of lung cancer in a subject in whom the levels of CEA antigen, CA125 antigen, CYFRA21-1 antigen, pro-SFTPB antigen, diacetylspermine (DAS) classifies the subject as having or being at risk of harboring lung cancer comprising one or more of: administering a chemotherapeutic drug to the subject with lung cancer; administering therapeutic radiation to the subject with lung cancer; and surgery for partial or complete surgical removal of cancerous tissue in the subject with lung cancer.

In another aspect, the invention provides a method for detecting and treating lung cancer, comprising: detecting CEA, CA125, CYFRA21-1, and pro-SFTPB, in a biological sample obtained from a human, via an immunoassay; quantifying the amounts CEA, CA125, CYFRA21-1, and pro-SFTPB in said collected sample; comparing the amounts of CEA, CA125, CYFRA21-1, and pro-SFTPB with a cutoff value to determine whether said human is at increased risk of having lung cancer or not; wherein if the levels are above the cutoff value said human has lung cancer, and administering a treatment for lung cancer to said human having lung cancer.

In another aspect, the invention provides a method of determining risk of a subject of harboring lung cancer, comprising: in biological samples from a subject in need of analysis, measuring the concentration of CEA, CA125, CYFRA21-1, and Pro-SFTPB; and comparing the concentration of the biomarkers in the samples of the subject in need of diagnosis and the concentration in a normal or non-diseased subject, wherein the subject in need of diagnosis is diagnosed with lung cancer, wherein the diagnosis is based on a cutoff value at a sensitivity or specificity value as set forth in Table 10.

In another aspect, the invention provides a method of determining evidence of lung cancer in a biological sample, comprising measuring the concentration of a biomarker panel comprising CEA, CA125, CYFRA21-1, Pro-SFTPB, and diacetylspermine (DAS), and identifiable parts thereof in a biological sample from a subject, wherein a change in the concentration of each of the biomarkers based on a sensitivity or specificity for a cutoff set forth in Table 10 is characteristic of lung cancer. In another embodiment, the levels of CEA, CA125, CYFRA21-1, and pro-SFTPB or the reporter molecules bound thereto are elevated in the subject relative to a healthy subject. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that does not have lung cancer. In another embodiment, the reference subject or group is healthy. In another embodiment, at least one of the surfaces further comprises at least one receptor molecule that selectively binds to a biomarker or antigen selected from CEA, CA125, CYFRA21-1, and Pro-SFTPB. In another embodiment, at least one of the surfaces is the surface of a solid particle. In another embodiment, the solid particle comprises a bead. In another embodiment, such methods comprising: measuring the level of diacetylspermine (DAS) in the biological sample; wherein the amount of diacetylspermine (DAS) classifies the patient as being at risk of harboring lung cancer or not at risk of harboring lung cancer. In another embodiment, the sample comprises a biological sample selected from blood, plasma, and serum. In another embodiment, the biological sample is serum. In another embodiment, the amount of CEA, CA125, CYFRA21-1, and pro-SFTPB is quantified. In another embodiment, detection of the amount of CEA, CA125, CYFRA21-1, pro-SFTPB, and diacetylspermine (DAS) comprises the use of a solid particle. In another embodiment, the solid particle is a bead. In another embodiment, at least one of the reporter molecules is linked to an enzyme. In another embodiment, at least one of the reporter molecules provides a detectable signal. In another embodiment, the detectable signal is detectable by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the concentrations of CEA, CA125, CYFRA21-1, Pro-SFTPB, and diacetylspermine (DAS) are measured. In another embodiment, the subject is determined to have lung cancer based on the measured concentrations of the biomarkers. In another embodiment, the measured concentrations are used to calculate a biomarker score based on sensitivity and specificity values at a cutoff set forth in Table 10. In another embodiment, such methods further comprise the steps of: comparing the measured concentrations of each biomarker in the biological sample to the prediction of a statistical model. In another embodiment, the panel is selected from the group consisting of: a. the panel consisting of CEA, CA125, CYFRA21-1, and Pro-SFTPB; or b. the panel consisting of CEA, CA125, CYFRA21-1, Pro-SFTPB, and diacetylspermine (DAS). In another embodiment, the panel comprises biomarkers that have been identified by a method selected from UV-visible spectroscopy, mass spectrometry, nuclear magnetic resonance (NMR) spectroscopy, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In another embodiment, the panel comprises biomarkers that have been identified by UV-visible spectroscopy or proton NMR spectroscopy. In another embodiment, the first reporter binds selectively to CEA. In another embodiment, the second reporter binds selectively to CA125. In another embodiment, the third reporter binds selectively to CYFRA21-1. In another embodiment, the fourth reporter binds selectively to Pro-SFTPB. In another embodiment, determination of CEA, CA125, CYFRA21-1, and pro-SFTPB levels is made at substantially the same time. In another embodiment, determination of CEA, CA125, CYFRA21-1, and pro-SFTPB levels is made in a stepwise manner. In another embodiment, such methods comprise inclusion of subject history information into the assignment of having lung cancer or not having lung cancer. In another embodiment, such methods comprise administering at least one alternate diagnostic test for a subject assigned as having lung cancer. In another embodiment, the at least one alternate diagnostic test comprises an assay or sequencing of at least one ctDNA.

In another embodiment, the method of treating a subject suspected of harboring lung cancer, comprising analyzing the subject for risk of harboring lung cancer with a method as described herein; and administering a therapeutically effective amount of a treatment for the cancer. In another embodiment, the treatment is surgery, chemotherapy, immunotherapy, radiation therapy, targeted therapy, or a combination thereof. In another embodiment, the classification of the subject as having lung cancer has a sensitivity of 0.76 and 0.42 at 78% and 94% specificity, respectively. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has adenocarcinoma. In another embodiment, the levels of CEA antigen, CA125 antigen, CYFRA21-1 antigen, and pro-SFTPB antigen are elevated in comparison to the levels of CEA antigen, CA125 antigen, CYFRA21-1 antigen, and pro-SFTPB antigen in a reference subject or group that has squamous cell cancer. In another embodiment, such methods further comprise comparing the amount of CEA, CA125, CYFRA21-1, and pro-SFTPB with a cutoff value as exemplified in Table 10. In another embodiment, the cutoff value comprises an AUC (95% CI) of at least 0.83. In another embodiment, the cutoff value comprises an AUC (95% CI) of at least 0.80. In another embodiment, the classification of the subject as having lung cancer has a sensitivity of 0.76 and 0.42 at 78% and 94% specificity, respectively. In another embodiment, the lung cancer is diagnosed at or before the borderline resectable stage. In another embodiment, the lung cancer is diagnosed at the resectable stage. In another embodiment, such methods further comprise: providing a surface that binds CEA, CA125, CYFRA21-1, and Pro-SFTPB; incubating the surface with the biological sample; contacting the surface with a first reporter molecule that binds CEA; contacting the surface with a second reporter molecule that binds CA125; contacting the surface with a third reporter molecule that binds CYFRA21-1; contacting the surface with a fourth reporter molecule that binds Pro-SFTPB; measuring the amount of the first reporter molecule that is associated with the surface; measuring the amount of the second reporter molecule that is associated with the surface; measuring the amount of the third reporter molecule that is associated with the surface; measuring the amount of the fourth reporter molecule that is associated with the surface; wherein the amount of the first reporter molecule, the second reporter molecule, the third reporter molecule, and the fourth reporter molecule classifies the subject as being at risk of harboring lung cancer or not at risk of harboring lung cancer.

In another aspect, the invention provides a kit for determining the presence of indicators of lung cancer in a sample from the subject comprising: (a) antigen-binding reagents that bind to each of the protein biomarkers selected from the group consisting of CEA, CA125, CYFRA21-1, and pro-SFTPB, or an array comprising said antigen-binding reagents; and (b) instructions for performing a method for determining the presence of lung cancer in an individual. In one embodiment, such a kit further comprises: a reagent solution that comprises a first solute for detection of CEA antigen; a second solute for detection of CA125 antigen; a third solute for detection of CYFRA21-1 antigen; a fourth solute for detection of pro-SFTPB antigen; and a fifth solute for detection of diacetylspermine (DAS). In another embodiment, such a kit comprises a device for contacting the reagent solutions with a biological sample. In another embodiment, such a kit comprises at least one surface with means for binding at least one biomarker or antigen. In another embodiment, the at least one biomarker or antigen is selected from the group consisting of CEA, CA125, CYFRA21-1, and pro-SFTPB. In another embodiment, the at least one surface comprises a means for binding ctDNA. In another embodiment, such a kit further comprises an antibody or antigen-binding fragment thereof that binds to the metabolite biomarker diacetylspermine (DAS). In another embodiment, the antigen-binding reagent comprises antibodies or antigen-binding fragments thereof, RNA, DNA, or RNA/DNA hybrids.

In another aspect, the invention provides a method comprising: a) obtaining a sample from a subject asymptomatic for lung cancer; b) measuring a panel of markers in the sample, wherein the markers comprise CEA, CA125, Cyfra 21-1, and diacetylspermine (DAS); c) determining a biomarker score for each marker; d) summing the biomarker scores for each marker to obtain a composite score for each subject, quantifying the increased risk for the presence of lung cancer for the subject as a risk score, wherein the composite score is matched to a risk category of a grouping of stratified subject populations, wherein each risk category comprises a multiplier indicating increased likelihood of having the lung cancer correlated to a range of composite scores as compared to use of a single threshold value, wherein the multiplier is determined from positive predictive scores of retrospective samples; and, e) administering a computerized tomography (CT) scan or other imagine modality to the subject with a quantified increased risk for the presence of lung cancer. In another embodiment, the markers consist of CEA, CA125, CYFRA21-1, Pro-SFTPB, and diacetylspermine (DAS). In another embodiment, the sample is blood, blood serum, blood plasma, or some part thereof. In another embodiment, the grouping of a stratified subject population, the multiplier indicating increased likelihood of having the cancer and the range of composite scores are determined from retrospective clinical samples of a population. In another embodiment, the risk category further comprises a risk identifier. In another embodiment, the risk identifier is selected from low risk, intermediate-low risk, intermediate risk, intermediate-high risk and highest risk. In another embodiment, calculating the multiplier indicating increased likelihood of having the cancer for each risk category comprises stratifying the subject cohort based on retrospective biomarker scores and weighting a known prevalence of the cancer in the cohort by a positive predictive score for each stratified population. In another embodiment, the grouping of a stratified subject population comprises at least three risk categories wherein the multiplier indicating increased likelihood of having cancer is about 2 or greater. In another embodiment, the grouping of a stratified subject population comprises at least two risk categories wherein the multiplier indicating increased likelihood of having cancer is about 5 or greater. In another embodiment, the subject is aged 50 years or older and has a history of smoking tobacco. In another embodiment, such methods further comprise generating a risk categorization table, wherein the panel of markers is measured, a biomarker score for each marker is determined, a composite score is obtained by summing the biomarker scores; determining a threshold value used to divide the composite scores into risk groups and assigning a multiplier to each group indicating the likelihood of an asymptomatic subject having a quantified increased risk for the presence of cancer. In another embodiment, the groups are in a form selected from an electronic table form, a software application, a computer program, and an excel spreadsheet. In another embodiment, the panel of markers comprise proteins, polypeptides, or metabolites measured in a binding assay. In another embodiment, the panel of markers comprise proteins or polypeptides measured using a flow cytometer.

Provided are methods for identifying lung cancer in a subject, the method generally comprising: (a) applying a blood sample obtained from the subject to analysis for four biomarkers: CEA, CA125, CYFRA21-1, and Pro-SFTPB; (b) quantifying the amount of the four biomarkers present in the blood sample; and (c) applying statistical analysis based on the amount of biomarkers present to determine a biomarker score with respect to corresponding lung cancer, thereby classifying a subject as either positive for lung cancer or negative for cancer.

The methods presented herein enable the screening of high-risk subjects, such as those with a family history of lung cancer, or subjects with other risk factors such as obesity, heavy smoking, and possibly diabetes. The logistic regression model disclosed herein can incorporate these factors into its classification method.

As used herein, "lung cancer status" refers to classification of an individual, subject, or patient as having lung cancer or as not having lung cancer. In some embodiments, an individual having lung cancer may be referred to as "lung cancer-positive." In other embodiments, an individual not having lung cancer may be referred to as "lung cancer-negative." For subjects that are classified as lung cancer-positive, further methods can be provided to clarify lung cancer status. Classification as lung cancer-positive can be followed by methods including, but not limited to, computed tomography (CT).

Detection of CEA can be accomplished by contact with a biomolecule with the sequence as laid out in SEQ ID NO.: 1.

Detection of CA125 can be accomplished by contact with a biomolecule with the sequence as laid out in SEQ ID NO.: 2.

Detection of CYFRA21-1 can be accomplished by contact with a biomolecule with the sequence as laid out in SEQ ID NO.: 3.

Detection of Pro-SFTPB can be accomplished by contact with a biomolecule with the sequence as laid out in SEQ ID NO.: 4.

A combination of at least the four biomarkers CEA, CA125, CYFRA21-1, and Pro-SFTPB can afford a previously unseen, highly reliable lung cancer predictive power. The integrated risk prediction model resulted in an AUC of 0.83 (95% CI: 0.77-0.89), compared to an AUC of 0.72 (95% CI: 0.65-0.79) of a model only including smoking information (p-value for difference in AUC: 0.001). At the USPSTF specificity of 0.78 (95% CI: 0.64-0.87), the sensitivity for the integrated risk prediction model was 0.76 (95% CI: 0.57-0.86), compared to 0.41 (95% CI: 0.28-0.66) for the smoking model. Conversely, at the USPSTF sensitivity of 0.42 (95% CI: 0.26-0.54), the specificity of the integrated risk-prediction model was 0.94 (95% CI: 0.88-0.98), compared to 0.78 (95% CI: 0.70-0.90) of the smoking model. These improvements in AUC, sensitivity and specificity estimates were consistently observed across relevant strata defined by sex and smoking status.

The disclosure is not limited to the specific biomolecules that are reported herein for detection of the biomarkers. Other molecules may be chosen for use in other embodiments, including, but not limited to, biomolecules based on proteins, antibodies, nucleic acids, aptamers, and synthetic organic compounds. Other molecules may demonstrate advantages in terms of sensitivity, efficiency, speed of assay, cost, safety, or ease of manufacture or storage.

In some embodiments, levels of CEA, CA125, CYFRA21-1, and Pro-SFTPB in a biological sample are measured. In some embodiments, CEA, CA125, CYFRA21-1, and Pro-SFTPB are contacted with reporter molecules, and the levels of respective reporter molecules are measured. In some embodiments, four reporter molecules are provided which specifically bind CEA, CA125, CYFRA21-1, and Pro-SFTPB, respectively. Use of reporter molecules can provide gains in convenience and sensitivity for the assay.

In some embodiments, CEA, CA125, CYFRA21-1, and Pro-SFTPB are adsorbed onto a surface that is provided in a kit. In some embodiments, reporter molecules bind to surface-adsorbed CEA, CA125, CYFRA21-1, and Pro-SFTPB. Adsorption of biomarkers can be nonselective or selective. In some embodiments, the surface comprises a receptor functionality for increasing selectivity towards adsorption of one or more biomarkers.

In some embodiments, CEA, CA125, CYFRA21-1, and Pro-SFTPB are adsorbed onto four surfaces that are selective for one or more of the biomarkers. A reporter molecule or multiple reporter molecules can then bind to surface-adsorbed biomarkers, and the level of reporter molecule(s) associated with a particular surface can allow facile quantification of the particular biomarker that is present on that surface.

In some embodiments, CEA, CA125, CYFRA21-1, and Pro-SFTPB are adsorbed onto a surface that is provided in a kit; relay molecules that are specific for one or more of these biomarkers bind to surface-adsorbed biomarkers; and receptor molecules that are specific for one or more relay molecules bind to relay molecules. Relay molecules can provide specificity for certain biomarkers, and receptor molecules can enable detection.

In some embodiments, four relay molecules are provided which specifically bind CEA, CA125, CYFRA21-1, and Pro-SFTPB, respectively. Relay molecules can be intentionally designed for specificity towards a biomarker, or can be selected from a pool of candidates due to their binding properties.

In some embodiments, CEA, CA125, CYFRA21-1, and Pro-SFTPB are adsorbed onto four discrete surfaces that are provided in a kit; relay molecules that are specific for one or more of these biomarkers bind to surface-adsorbed biomarkers; and receptor molecules bind to relay molecules. Analysis of the surfaces can be accomplished in a stepwise or concurrent fashion.

In some embodiments, the reporter molecule is linked to an enzyme, facilitating quantification of reporter molecule. In some embodiments, quantification can be achieved by catalytic production of a substance with desirable spectroscopic properties.

In some embodiments, the amount of biomarker is determined with spectroscopy. In some embodiments, the spectroscopy that is utilized is UV-visible spectroscopy. In some embodiments, the spectroscopy that is utilized is mass spectrometry. In other embodiments, the spectroscopy that is utilized is nuclear magnetic resonance (NMR) spectroscopy, such as including, but not limited to, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry.

The quantity of biomarker or biomarkers that is found in a particular assay can be directly reported to an operator, or alternately it can be stored digitally and readily made available for mathematical processing. A system can be provided for performing mathematical analysis, and can further report classification as lung cancer-positive or lung cancer-negative to an operator.

In some embodiments, additional assays known to those of ordinary skill in the art can function with the disclosure herein. Other assays include, but are not limited to, assays utilizing mass-spectrometry, immunoaffinity LC-MS/MS, surface plasmon resonance, chromatography, electrochemistry, acoustic waves, immunohistochemistry and array technologies.

In certain embodiments, the lung cancer is non-small call lung cancer (NSCLC).

The various system components discussed herein may include one or more of the following: a computer comprising one or more processors for processing digital data; short- or long-term digital memory; an input analog-to-digital converter for providing digitized data; an application program made available to the processor for directing processing of digital data by the processor; an input device for collecting information from the subject or operator, and an output device for displaying information to the subject or operator.

Also provided herein are methods of treatment for subjects who are classified as lung cancer-positive. Treatment for lung cancer-positive patients can include, but is not limited to, surgery, chemotherapy, radiation therapy, targeted therapy, or a combination thereof.

With regard to the detection of the biomarkers detailed herein, the disclosure is not limited to the specific biomolecules reported herein. In some embodiments, other biomolecules can be chosen for the detection and analysis of the disclosed biomarkers including, but not limited to, biomolecules based on proteins, antibodies, nucleic acids, aptamers, and synthetic organic compounds. Other molecules may demonstrate advantages in terms of sensitivity, efficiency, speed of assay, cost, safety, or ease of manufacture or storage. In this regard, those of ordinary skill in the art will appreciate that the predicative and diagnostic power of the biomarkers disclosed herein may extend to the analysis of not just the protein form of these biomarkers, but other representations of the biomarkers as well (e.g., nucleic acid). Further, those of ordinary skill in the art will appreciate that the predicative and diagnostic power of the biomarkers disclosed herein can also be used in combination with an analysis of other biomarkers associated with lung cancer. In some embodiments, other biomarkers associated with lung cancer can be protein-based biomarkers. In some embodiments, other biomarkers associated with lung cancer can be non-protein-based biomarkers, such as, for instance, ctDNA.

The foregoing has outlined rather broadly the features and technical benefits of the disclosure in order that the detailed description may be better understood. It should be appreciated by those skilled in the art that the specific embodiments disclosed may be readily utilized as a basis for modifying or designing other structures or processes for carrying out the same purposes of the disclosure. It is to be understood that the present disclosure is not limited to the particular embodiments described, as variations of the particular embodiments may be made and still fall within the scope of the appended claims.

Definitions

As used herein, the term "lung cancer" refers to a malignant neoplasm of the lung characterized by the abnormal proliferation of cells, the growth of which cells exceeds and is uncoordinated with that of the normal tissues around it.

As used herein, the term "lung cancer-positive" refers to classification of a subject as having lung cancer.

As used herein, the term "lung cancer-negative" refers to classification of a subject as not having lung cancer.

As used herein, the terms "subject" or "patient" refer to a mammal, preferably a human, for whom a classification as lung cancer-positive or lung cancer-negative is desired, and for whom further treatment can be provided.

As used herein, a "reference patient," "reference subject," or "reference group" refers to a group of patients or subjects to which a test sample from a patient or subject suspected of having or being at risk of harboring lung cancer may be compared. In some embodiments, such a comparison may be used to determine whether the test subject has lung cancer. A reference patient or group may serve as a control for testing or diagnostic purposes. As described herein, a reference patient or group may be a sample obtained from a single patient, or may represent a group of samples, such as a pooled group of samples.

As used herein, "healthy" refers to an individual in whom no evidence of lung cancer is found, i.e., the individual does not have lung cancer. Such an individual may be classified as "lung cancer-negative" or as having healthy lungs, or normal, non-compromised lung function. A healthy patient or subject has no symptoms of lung cancer or other lung disease. In some embodiments, a healthy patient or subject may be used as a reference patient for comparison to diseased or suspected diseased samples for determination of lung cancer in a patient or a group of patients.

As used herein, the terms "treatment" or "treating" refer to the administration of medicine or the performance of medical procedures with respect to a subject, for either prophylaxis (prevention) or to cure or reduce the extent of or likelihood of occurrence or recurrence of the infirmity or malady or condition or event in the instance where the subject or patient is afflicted. As related to the present disclosure, the term may also mean the administration of pharmacological substances or formulations, or the performance of non-pharmacological methods including, but not limited to, radiation therapy and surgery. Pharmacological substances as used herein may include, but are not limited to, chemotherapeutics that are established in the art, such as Erlotinib (TARCEVA and others), Afatinib (GILOTRIF), Gefitinib (IRESSA), Bevacizumab (AVASTIN), Crizotinib (XALKORI), Ceritinib (ZYKADIA). cisplatin (PLATINOL), carboplatin (PARAPLATIN), docetaxel (TAXOTERE), gemcitabine (GEMZAR), paclitaxel (TAXOL and others), vinorelbine (NAVELBINE and others), or pemetrexed (ALIMTA). Pharmacological substances may include substances used in immunotherapy, such as checkpoint inhibitors. Treatment may include a multiplicity of pharmacological substances, or a multiplicity of treatment methods, including, but not limited to, surgery and chemotherapy.

As used herein, the term "CARET" refers to the Beta-Carotene and Retinol Efficacy Trial study.

As used herein, the term "NLST" refers to National Lung Screening Trial.

As used herein, the term "USPSTF" refers to the US Preventive Services Task Force.

As used herein, the term "EPIC" refers to European Prospective Investigation into Cancer and Nutrition.

As used herein, the term "NSHDS" refers to the Northern Sweden Health and Disease Study.

As used herein, the term "ICD-O-2" refers to the International Classification of Diseases for Oncology, Second Edition.

As used herein, the term "ELISA" refers to enzyme-linked immunosorbent assay. This assay generally involves contacting a fluorescently tagged sample of proteins with antibodies having specific affinity for those proteins. Detection of these proteins can be accomplished with a variety of means, including but not limited to laser fluorimetry.

As used herein, the term "regression" refers to a statistical method that can assign a predictive value for an underlying characteristic of a sample based on an observable trait (or set of observable traits) of said sample. In some embodiments, the characteristic is not directly observable. For example, the regression methods used herein can link a qualitative or quantitative outcome of a particular biomarker test, or set of biomarker tests, on a certain subject, to a probability that said subject is for lung cancer-positive.

As used herein, the term "logistic regression" refers to a regression method in which the assignment of a prediction from the model can have one of several allowed discrete values. For example, the logistic regression models used herein can assign a prediction, for a certain subject, of either lung cancer-positive or lung cancer-negative.

As used herein, the term "biomarker score" refers to a numerical score for a particular subject that is calculated by inputting the particular biomarker levels for said subject to a statistical method.

As used herein, the term "composite score" refers to a summation of the normalized values for the predetermined markers measured in the sample from the subject. In one embodiment, the normalized values are reported as a biomarker score and those biomarker score values are then summed to provide a composite score for each subjected tested. When used in the context of the risk categorization table and correlated to a stratified grouping based on a range of composite scores in the Risk Categorization Table, the "composite score" is used to determine the "risk score" for each subject tested wherein the multiplier indicating increased likelihood of having the cancer for the stratified grouping becomes the "risk score".

As used herein, the term "risk score" refers to a single numerical value that indicates an asymptomatic human subject's increased risk for harboring a cancer as compared to the known prevalence of cancer in the disease cohort. In certain embodiments, the composite score as calculated for a human subject and correlated to a multiplier indicating increased risk of harboring the cancer, wherein the composite score is correlated based on the range of composite scores for each stratified grouping in the risk categorization table. In this way the composite score is converted to a risk score based on the multiplier indicating increased likelihood of having the cancer for the grouping that is the best match for the composite score.

As used herein, the term "cutoff" or "cutoff point" refers to a mathematical value associated with a specific statistical method that can be used to assign a classification of lung cancer-positive of lung cancer-negative to a subject, based on said subject's biomarker score.

As used herein, when a numerical value above or below a cutoff value "is characteristic of lung cancer," what is meant is that the subject, analysis of whose sample yielded the value, either has lung cancer or is at risk of harboring lung cancer.

As used herein, a subject who is "at risk of harboring lung cancer" is one who may not yet evidence overt symptoms of lung cancer, but who is producing levels of biomarkers which indicate that the subject has lung cancer, or may develop it in the near term. A subject who has lung cancer or is suspected of harboring lung cancer may be treated for the cancer or suspected cancer.

As used herein, the term "classification" refers to the assignment of a subject as either lung cancer-positive or lung cancer-negative, based on the result of the biomarker score that is obtained for said subject.

As used herein, the term "lung cancer-positive" refers to an indication that a subject is predicted as at risk of harboring lung cancer, based on the results of the outcome of the methods of the disclosure.

As used herein, the term "lung cancer-negative" refers to an indication that a subject is predicted as not at risk of harboring lung cancer, based on the results of the outcome of the methods of the disclosure.

As used herein, the term "Wilcoxon rank sum test," also known as the Mann-Whitney U test, Mann-Whitney-Wilcoxon test, or Wilcoxon-Mann-Whitney test, refers to a specific statistical method used for comparison of two populations. For example, the test can be used herein to link an observable trait, in particular a biomarker level, to the absence or presence of lung cancer in subjects of a certain population.

As used herein, the term "true positive rate" refers to the probability that a given subject classified as positive by a certain method is truly positive.

As used herein, the term "false positive rate" refers to the probability that a given subject classified as positive by a certain method is truly negative.

As used herein, the term "sensitivity" refers to, in the context of various biochemical assays, the ability of an assay to correctly identify those with a disease (i.e., the true positive rate). By comparison, as used herein, the term "specificity" refers to, in the context of various biochemical assays, the ability of an assay to correctly identify those without the disease (i.e., the true negative rate). Sensitivity and specificity are statistical measures of the performance of a binary classification test (i.e., classification function). Sensitivity quantifies the avoiding of false negatives, and specificity does the same for false positives.

As used herein, a "sample" refers to a test substance to be tested for the presence of, and levels or concentrations thereof, of a biomarker as described herein. A sample may be any substance appropriate in accordance with the present disclosure, including, but not limited to, blood, blood serum, blood plasma, or any part thereof.

As used herein, an "antigen" refers to a protein, metabolite, or other molecule to which an antibody or antigen-binding reagent or fragment may bind for detection of a biomarker as described herein. In some embodiments, a biomarker may serve as an antigen. In other embodiments, a portion of a biomarker may serve as an antigen. In some embodiments, an antibody may be used for detection of an antigen as described herein. In other embodiments, a nucleic acid, such as DNA, RNA, DNR/RNA hybrids, antibodies, antibody fragments, or any other compound or molecule capable of binding to an antigen, may be used to detect an antigen, such as a biomarker as described herein. An antigen as described herein may serve as the basis for detection of the levels, concentrations, or amounts of a protein or metabolite marker for use with the methods as described herein.

As used herein, the term "CEA" refers to carcinoembryonic antigen.

As used herein, the term "CA125" refers to cancer antigen 125.

As used herein, the term "CYFRA21-1," also known as Cyfra 21-1, refers to cytokeratin fragment 19, also known as cytokeratin-19 fragment.

As used herein, the term "SFTPB" refers to Surfactant Protein B.

As used herein, the term "Pro-SFTPB," refers to Pro-Surfactant Protein B, which is a precursor form of SFTPB.

As used herein, the term "HE4," also known as WFDC2, refers to human epididymis protein 4.

As used herein, the term "ctDNA" refers to cell-free or circulating tumor DNA. ctDNA is tumor DNA found circulating freely in the blood of a cancer patient. Without being limited by theory, ctDNA is thought to originate from dying tumor cells and can be present in a wide range of cancers but at varying levels and mutant allele fractions. Generally, ctDNA carry unique somatic mutations formed in the originating tumor cell and not found in the host's healthy cells. As such, the ctDNA somatic mutations can act as cancer-specific biomarkers.

As used herein, a "metabolite" refers to small molecules that are intermediates and/or products of cellular metabolism. Metabolites may perform a variety of functions in a cell, for example, structural, signaling, stimulatory and/or inhibitory effects on enzymes. In some embodiments, a metabolite may be a non-protein, plasma-derived metabolite marker, such as including, but not limited to, acetylspermidine, diacetylspermine, lysophosphatidylcholine (18:0), lysophosphatidylcholine (20:3), and an indole-derivative.

As used herein, the term "ROC" refers to receiver operating characteristic, which is a graphical plot used herein to gauge the performance of a certain diagnostic method at various cutoff points. A ROC plot can be constructed from the fraction of true positives and false positives at various cutoff points.

As used herein, the term "AUC" refers to the area under the curve of the ROC plot. AUC can be used to estimate the predictive power of a certain diagnostic test. Generally, a larger AUC corresponds to increasing predictive power, with decreasing frequency of prediction errors. Possible values of AUC range from 0.5 to 1.0, with the latter value being characteristic of an error-free prediction method.

As used herein, the term "p-value" or "p" refers to the probability that the distributions of biomarker scores for lung cancer-positive and lung cancer-negative subjects are identical in the context of a Wilcoxon rank sum test. Generally, a p-value close to zero indicates that a particular statistical method will have high predictive power in classifying a subject.

As used herein, the term "CI" refers to a confidence interval, i.e., an interval in which a certain value can be predicted to lie with a certain level of confidence. As used herein, the term "95% CI" refers to an interval in which a certain value can be predicted to lie with a 95% level of confidence.

The term "AIC" refers to Akaike Information Criterion, a method based on information theory that can be used to evaluate the relative merits of various regression models for a dataset.

EXAMPLES

The following examples are included to demonstrate embodiments of the disclosure. The following examples are presented only by way of illustration and to assist one of ordinary skill in using the disclosure. The examples are not intended in any way to otherwise limit the scope of the disclosure. Those of skill in the art should, in light of the present disclosure, appreciate that many changes can be made in the specific embodiments which are disclosed and still obtain a like or similar result without departing from the spirit and scope of the disclosure.

Example 1: Blood Sample Sets

Plasma samples from all study participants were sent on dry ice to the laboratory at MD Anderson, TX, US, where they were kept below −80° C. until analysis.
Training Cohort: The Beta-Carotene and Retinol Efficacy Trial (CARET) Study.

Pre-diagnostic serum samples from CARET participants (current or former heavy smokers) were utilized to train the biomarker score of potential protein-based risk prediction markers. CARET was a randomized, double-blind, placebo-controlled trial evaluating the cancer prevention efficacy and the safety of daily supplementation with 30 mg of beta-carotene and 25,000 IU retinol palmitate in 18,314 persons with high risk for lung cancer. Eligible participants included two high-risk populations: 14,254 men and women aged 50 to 69 years who were current or former smokers (quit within the previous 6 years) who were exposed to at least 20 pack-years of cigarette smoking, and 4,060 men aged 45 to 69 years who were current or former smokers (quit no more than 15 years prior to the start of the study) and had a substantial history of occupational asbestos exposure. Participants were enrolled in 6 US centers from 1985 to 1994 and were followed for cancer and mortality outcomes until 2005. In total, samples were assayed from 108 subjects who subsequently developed non-small-cell lung cancer (NSCLC) within 12 months after providing a blood sample, and 216 controls matched to each case based on age at baseline (5-yr groups), sex, baseline smoking status (current vs former), and study enrollment period.

Pre-diagnostic serum samples from CARET participants (current or former heavy smokers), consisting of 108 subjects who subsequently developed non-small-cell lung cancer (NSCLC) and 216 matched controls were utilized to test a set of potential protein-based risk prediction markers including Pro-SFTPB. None of these samples were part of any prior assays of the candidate markers to be tested and thus represented an independent set for marker assays consisting of 108 NSCLC and 216 matched controls. Case samples were collected up to a year prior to a diagnosis of NSCLC.

Validation Cohort: The EPIC and NSHDS Studies.

The validation cohort used in this study were obtained from two European prospective studies: the European Prospective Investigation into Cancer and Nutrition (EPIC) study and The Northern Sweden Health and Disease Study (NSHDS).

European Prospective Investigation into Cancer and Nutrition

The EPIC study is an ongoing multi-center prospective cohort that recruited 521,330 participants between 1992 and 1998 from 23 centers across ten countries in Europe. The current biomarker study involved EPIC participants from 7 countries (Greece, Netherlands, UK, France, Germany, Spain, and Italy) who donated a blood sample at study recruitment that was part of a biorepository maintained in liquid nitrogen at the International Agency for Research on Cancer (IARC) in Lyon.

Northern Sweden Health and Disease Study

NSHDS is an ongoing prospective cohort of the general population of the Västerbotten County in northern Sweden. After study initiation in 1985, all county residents have since been invited to participate by attending a health check-up at 40, 50, and 60 years of age. As of 2014, the cohort had recruited 99,404 study participants who donated a blood sample for future research. Details on EPIC and NSHDS recruitment procedures, collection of questionnaire and anthropometric data, and blood sample collection and storage have been described in detail elsewhere. Characteristics for the EPIC and NSHDS validation cohorts are presented below in Table 1.

The baseline characteristics of cases and controls in the CARET training study and the EPIC and NSHDS validation studies are presented in Table 1. The characteristics of the EPIC and NSHDS study sample used to train the smoking model are presented in Table 2.

TABLE 1

Clinical characteristics of patients and controls in training and validation cohorts.

| | | Training study (CARET) | | Validation study (EPIC and NSHDS) | |
|---|---|---|---|---|---|
| | N (%) | Cases | Controls | Cases | Controls |
| Overall | | 108 | 216 | 83 | 158 |
| Sex | Male | 75 (69.4) | 150 (69.4) | 50 (60.2) | 93 (58.9) |
| | Female | 33 (30.6) | 66 (30.6) | 33 (39.8) | 65 (41.1) |
| Race | White | 99 | 200 | | |
| | Black | 6 | 8 | | |
| | Other | 3 | 8 | | |
| Age, years | ≤40 | — | — | 3 (3.6) | 6 (3.8) |
| | 40-50 | 2 (1.9) | 4 (1.9) | 7 (8.4) | 13 (8.2) |
| | 50-60 | 35 (32.4) | 72 (33.3) | 40 (48.2) | 78 (49.4) |
| | 60-70 | 69 (63.9) | 136 (63.0) | 29 (34.9) | 54 (34.2) |
| | >70 | 2 (1.9) | 4 (1.9) | 4 (4.8) | 7 (4.4) |
| Pack-years | Mean | 54 | 49 | | |
| | SD | 23 | 20 | | |
| Age at diagnosis, years | Mean | 65.1 | | | |
| | SD | 6.3 | | | |
| | ≤40 | — | — | | |
| | 40-50 | 2 | 4 | | |
| | 50-60 | 35 | 72 | | |
| | 60-70 | 69 | 136 | | |
| | >70 | 2 | 4 | | |
| Yeas from blood collection to diagnosis | 0-0.5 | 40 (37.0) | — | 31 (37.3) | — |
| | 0.5-1 | 68 (63.0) | — | 33 (39.8) | — |
| | 1-2 | — | — | 19 (22.9) | — |
| | 2-5 | — | — | — | — |
| | 5-10 | — | — | — | — |
| Smoking status | Never | — | — | 9 (10.8) | 50 (31.7) |
| | Former | 36 (33.3) | 72 (33.3) | 26 (31.3) | 53 (33.5) |
| | Current | 72 (66.7) | 144 (66.7) | 48 (57.8) | 55 (34.8) |
| Histological subtype | ADC | 40 (37.0) | — | 32 (38.6) | — |
| | SCC | 38 (35.2) | — | 21 (25.3) | — |
| | Other | 30 (27.8) | — | 30 (36.1) | — |
| Stage | I and II | 26 | | | |
| | III and IV | 64 | | | |
| | Unknown | 18 | | | |
| Eligible for lung cancer screening (USPSTF) | Not Eligible | 29 (26.9) | 57 (26.4) | 51 (63.0) | 132 (85.2) |
| | Eligible | 79 (73.1) | 159 (73.6) | 30 (37.0) | 23 (14.8) |
| | N/A | — | — | 2 | 3 |

Abbreviations: NSCLC, non-small cell lung cancer;
SCC, squamous cell carcinoma;
ADC Adenocarcinoma;
SD, standard deviation

TABLE 2

Baseline characteristics of the EPIC and NSHDS study with that were used to train the smoking-model.

| | | Training sample for the smoking-model (EPIC + NSHDS) | |
|---|---|---|---|
| | N (%) | Cases | Controls |
| Overall | | 1008 | 1873 |
| Sex | Male | 605 (60) | 1088 (58.1) |
| | Female | 403 (40) | 785 (41.9) |
| Age, years | ≤40 | 20 (2.0) | 45 (2.4) |
| | 40-50 | 167 (16.6) | 315 (16.8) |
| | 50-60 | 430 (42.7) | 787 (42.0) |
| | 60-70 | 315 (31.2) | 599 (32.0) |
| | >70 | 76 (7.5) | 127 (6.8) |
| Yeas from blood collection to diagnosis | 0-0.5 | — | — |
| | 0.5-1 | — | — |
| | 1-2 | — | — |
| | 2-5 | 351 (34.8) | — |
| | 5-10 | 657 (65.2) | — |
| Smoking status | Never | 122 (12.1) | 524 (28.0) |
| | Former | 296 (29.4) | 606 (32.3) |
| | Current | 590 (58.5) | 743 (39.7) |

TABLE 2-continued

Baseline characteristics of the EPIC and NSHDS study with that were used to train the smoking-model.

| | N (%) | Training sample for the smoking-model (EPIC + NSHDS) | |
|---|---|---|---|
| | | Cases | Controls |
| Histological subtype | Adenocarcinoma | 366 (36.3) | — |
| | Squamous cell carc. | 200 (19.8) | — |
| | Other | 442 (43.6) | |
| Eligible for lung cancer screening (USPSTF) | Not Eligible | 688 (68.7) | 1599 (86.6) |
| | Eligible | 313 (31.3) | 248 (13.4) |
| | N/A | 7 | 26 |

Follow-Up and Selection of Cases and Controls

Follow-up for incident cancer cases was performed using a combination of methods, including record linkage with regional or national cancer registries, as well as health insurance records, cancer and pathology registries, and active follow-up through study subjects and their next-of-kin. Lung cancer cases were defined on the basis of the International Classification of Diseases for Oncology, Second Edition (ICD-O-2), and included all invasive cancers that were coded as C34. After excluding cases who had a history of another cancer (except non-melanoma skin cancer) and cases with missing blood samples or smoking information, 48 incident cases diagnosed within 1 year of blood draw in EPIC and 35 incident cases diagnosed within 2 years of blood draw in NSHDS were available for the current study. In Italy, the Netherlands, Spain, Sweden, and the UK, incident cancer cases were identified through record linkage with regional or national cancer registries. In France, Germany, and Greece, follow-up was based on a combination of methods, including health insurance records, cancer and pathology registries, and active follow-up through study subjects and their next-of-kin.

For each index case, two controls were chosen at random from risk sets consisting of all cohort members alive and free of cancer (except non-melanoma skin cancer) at the time of diagnosis of the index case. Matching criteria were study center, sex, date of blood collection (±1 month, relaxed to ±12 months for sets without available controls), time at blood collection (±1 hour, relaxed to ±12 hours), and age at blood collection (±3 months, relaxed to ±5 years). In order to improve the statistical power in smoking stratified analyses, each one of the controls was additionally matched based on smoking status of the index case from 5 categories; never smokers, short and long term quitters among former smokers (<10 years, ≥10 years since quitting), and light and heavy smokers among current smokers (<15 years, ≥15 cigarettes per day).

The final combined validation study from EPIC (cases diagnosed within 1 year of blood draw) and NSHDS (cases diagnosed within 2 years of blood draw) included 83 incident lung cancer cases and 158 matched controls. All study participants gave written informed consent to participate in the study and the research was approved by the local ethics committees in the participating countries, as well as the IARC and MD Anderson Ethical Review Committees.

For each EPIC and NSHDS index case, two controls were chosen at random from risk sets consisting of all cohort members alive and free of cancer (except non-melanoma skin cancer) at the time of diagnosis of the index case. For each case, one control was randomly chosen from risk-sets consisting of all cohort members alive and free of cancer (except non-melanoma skin cancer) at the time of diagnosis of the index case. Matching criteria were study center, sex, date of blood collection (±1 month, relaxed to ±3 months for sets without available controls), and date of birth (±1 year, relaxed to ±3 years). In order to improve the statistical power in smoking stratified analyses, one of the controls was additionally matched on the smoking status of the index case from 5 categories; never smokers, short and long term quitters among former smokers (<10 years, ≥10 years since quitting), and light and heavy smokers among current smokers (<15 years, ≥15 cigarettes per day).

The total combined validation cohort from EPIC and NSHDS included 74 incident lung cancer cases and 109 matched controls after excluding never smoking cases and controls. All participants gave written informed consent to participate in the study and the research was approved by the local ethics committees in the participating countries and the IARC Institutional Review Board.

Example 2: Selection of Biomarker Panel Candidates

Initial screening of biomarkers was performed on a set of five candidates: CEA, CA125, CYFRA 21-1, Pro-SFTPB, and HE4. CEA and CA125 are well-known tumor biomarkers and routinely used as prognostic and diagnostic markers of colorectal and ovarian cancer, respectively. CYFRA 21-1 has since the 90s been implicated as a marker of non-small cell lung cancer. SFTPB and HE4 are significantly associated with lung cancer both in mouse models of lung cancer and in blood samples collected up to one year prior to clinical diagnosis, compared to matched controls (Bach et al., J Natl Cancer Inst 95:470-8, 2003). A precursor form of SFTPB (Pro-SFTPB) was predictive of lung cancer risk in prospective cohort studies that encompassed the Pan-Canadian Early Detection of Lung Cancer Study, The Physicians' Health Study, and the CARET study (Cassidy et al., Br J Cancer 98:270-6, 2008; Hoggart et al., Cancer Prev Res (Phila) 5:834-46, 2012; Spitz et al., Cancer Prev Res (Phila) 1:250-4, 2008). Pro-SFTPB was originally found elevated in plasma of mice with lung cancer.

From this set, four biomarkers were selected for a panel based on their performance in the training cohort: CA-125, CYFRA 21-1, CEA, and Pro-SFTPB.

Observed levels of biomarkers for the control population are set forth in Table 3. Typical ranges for these values in healthy subjects are also provided.

TABLE 3

Observed biomarker levels in control population.

| Biomarker | Min* | Median | Max | Typical range |
|---|---|---|---|---|
| CEA | 0.47 | 1.96 | 10 | 0-5 |
| CA125 | 4.33 | 6.7 | 12.13 | 0-35 |
| CYFRA | 2.51 | 4.24 | 15.89 | 0.16-2.95 |
| Pro-SFTPB | 0 | 5.2 | 93.23 | N/A |

*Units in ng/mL for CEA, CYFRA, and Pro-SFTPB; Units in U/mL for CA125.

Observed levels of biomarkers for the cancer population are set forth in Table 4. Typical ranges for these values in cancer-afflicted subjects are also provided.

TABLE 4

Observed biomarker levels in cancer population.

| Biomarker | Min* | Median | Max | Typical range |
|---|---|---|---|---|
| CEA | 0.62 | 9.26 | 120.6 | 0-20 |
| CA125 | 4.24 | 7.29 | 20.51 | >35 |
| CYFRA | 3.3 | 5.66 | 20.93 | 0.93-221.6 |
| Pro-SFTPB | 1.08 | 22.66 | 233.11 | N/A |

*Units in ng/mL for CEA, CYFRA, and Pro-SFTPB; Units in U/mL for CA125.

Example 3: Analysis of Samples

The five candidate markers were analyzed by immunoassay using serum samples from the training cohort. Concentrations for CA125, CEA, Pro-SFTPB, CYFRA 21-1 and HE4 were determined using bead-based immunoassays on the MAGPIX® instrument (Luminex Corporation, Austin TX). Samples were analyzed in batches of 36 samples in duplicates, and quality control procedures included 7 calibration samples, 2 quality control samples, and 1 blank sample in each batch. The coefficients of variation (CVs) within and between batches were, respectively, 6.86% and 15.54% for CA125, 1.45% and 9.32% for CEA, 6.55% and 17.26% for Pro-SFTPB, and 5.56% and 28.71% for CYFRA 21-1. All lung cancer cases and their individually matched controls were analyzed together within the same batches in random order. The laboratory staff was blinded to the case-control status of the blood samples.

Example 4: Regression Model

Each evaluated biomarker was initially log-transformed and standardized within each study sample separately. The biomarkers CA125, CEA, Pro-SFTPB, and CYFRA were combined into a biomarker-based risk score (biomarker-score) by fitting logistic regression models. CYFRA in CARET2 was lacking data for 47.53% of samples. In order to use as many observations as possible for model building, a two-stage method was employed: in the first stage, an optimal biomarker panel was selected based on the Akaike Information Criterion by using all biomarkers apart from CYFRA using logistic regression; in the second stage, the combined score from the first stage was fixed and combined with CYFRA to obtain the final model. Such two-stage method allows observations to also contribute to model training. All inference is based on the bootstrap that employs 1000 samples with replacement separately for the healthy and the diseased.

In order to evaluate the extent to which the biomarker score could improve on a risk prediction model based on smoking exposure history, we fitted a smoking-model using data from EPIC and NSHDS that were not used in the validation study, defined by cases diagnosed 2 to 10 years after study recruitment with controls individually matched with the same matching criteria as in the validation study (1,008 cases and 1,873 controls. With use of conditional logistic regression and conditioning on the individual case-sets, the smoking-model included smoking status (former vs. never, current vs. never), number of cigarettes per day for current smokers (continuous [not available in former smokers]), smoking duration (continuous in former and current smokers), and time since quitting in former smokers [continuous].

We evaluated the biomarker-score for its potential to improve a risk prediction model based on smoking variables alone using the combined EPIC and NSHDS sample, first by fitting a model (smoking model) including smoking variables using unconditional logistic regression. This model included age (continuous), sex (dichotomous), cohort (dichotomous), smoking status (former/current), cigarettes per day in current smokers (continuous [not available in former smokers]), smoking duration (continuous), and time since quitting in former smokers [continuous]. Parameter estimates for the smoking model are presented in Table 5.

The extent to which the biomarker score and smoking-model could discriminate between incident lung cancer cases and controls was subsequently evaluated externally and non-parametrically by assigning the respective models to each participant in the validation study (cases diagnosed 0 to 2 years after blood draw). In addition, in order to evaluate the potential of combining the biomarker score with the smoking-model, an integrated risk prediction model was developed by fitting a conditional logistic regression model using the smoking model-based risk score and biomarker score as two separate covariates in the validation study.

TABLE 5

Specifications of the smoking model developed in EPIC and NSHDS based on cases diagnosed between 2 to 10 years from blood draw.

| Variables included in the smoking score | Beta estimates for the smoking-score | OR | 95% CI |
|---|---|---|---|
| Former vs never | 1.417089 | 4.13 | [2.73-6.22] |
| Current vs never | 2.084509 | 8.04 | [5.45-11.9] |
| Duration of smoking (years) among ever smokers | 0.038906 | 1.04 | [1.02-1.06] |
| Time since smoking cessation (years) for former smokers | −0.027166 | 0.97 | [0.95-0.99] |
| Number of cigarette smoked per day for current smokers | 0.066884 | 1.07 | [1.05-1.09] |

The coefficients of the logarithm of the biomarker concentrations were as follows: CA-125, 0.4730; CYFRA 21-1, 0.2612; CEA, 0.6531; and Pro-SFTPB, 0.9238; constant, −8.4927.

$$\log \mathrm{it}(p) = -8.4927 + 0.4730 \times \log CA125 + 0.2612 \times \log CYFRA211 + 0.6531 \times \log CEA + 0.9238 \times \log \mathrm{ProSFTPB}$$

Example 5: Performance of Regression Model

Each candidate biomarker discriminated between cases and controls in the CARET training study (p-value <0.05), with AUC estimates ranging from 0.60 (95% CI: 0.53-0.67, CA125) to 0.70 (95% CI: 0.64-0.76, Pro-SFTPB) (Table 6). Based on AIC, HE4 was excluded from the model, and the final biomarker score was defined by CA125, CEA, Pro-SFTBP and CYFRA 21-1 and yielded an overall AUC of 0.80 (95% CI 0.72-0.87) in the training sample (FIG. 1).

TABLE 6

Individual biomarker performance.

| | Discriminative performance | | Sensitivity at 95% Specificity | Specificity at 95% Sensitivity | Model specification | |
|---|---|---|---|---|---|---|
| | AUC | 95% CI | | | Beta-estimate | 95% CI |
| CA125 | 0.597 | [0.53-0.67] | 0.1250 | 0.0979 | 0.4730 | [0.0886-0.08583] |
| CEA | 0.688 | [0.62-0.75] | 0.2708 | 0.1563 | 0.6531 | [0.1364-1.1698] |
| Pro-SFTPB | 0.704 | [0.64-0.76] | 0.1667 | 0.2272 | 0.9238 | [0.3627-1.4849] |
| CYFRA21-1 | 0.658 | [0.56-0.75] | 0.1042 | 0.1672 | 0.2612 | [−0.1601-0.6825] |
| HE4 | 0.645 | [0.58-0.71] | 0.1262 | 0.1053 | N/A | |

The biomarker score discriminated similarly for the two most prevalent histologic types of lung cancer in the training study, with an AUC of 0.79 for lung adenocarcinoma (95% CI: 0.67-0.92) and 0.79 in lung squamous carcinoma (95% CI: 0.62-0.96) (Table 7). The AUC was higher for lung cancer cases diagnosed within 6 months of blood draw (AUC: 0.86, 95% CI: 0.76-0.96) compared to cases diagnosed between 6 months and 12 months after blood draw (AUC: 0.77, 95% CI: 0.66-0.88) (Table 7).

TABLE 7

Performance of the biomarker score in the CARET training study

| | AUC | 95% CI | p value | Sensitivity at 95% Specificity | Specificity at 95% Sensitivity |
|---|---|---|---|---|---|
| ALL individuals | 0.798 | 0.72 0.87 | <0.0001 | 0.2000 | 0.1875 |
| Men | 0.783 | 0.68 0.88 | <0.0001 | 0.2581 | 0.1486 |
| Women | 0.829 | 0.70 0.96 | <0.0001 | 0.1429 | 0.2105 |
| Stage I-II | 0.677 | 0.45 0.90 | 0.0599 | 0.2000 | 0.1538 |
| Stage III-IV | 0.831 | 0.75 0.91 | <0.0001 | 0.1724 | 0.5857 |
| Time between blood draw and diagnostic: | | | | | |
| 0-6 months | 0.858 | 0.76 0.96 | <0.0001 | 0.3810 | 0.6957 |
| 6-12 months | 0.770 | 0.66 0.88 | <0.0001 | 0.2083 | 0.1667 |
| Histological subtype: | | | | | |
| ADC* | 0.794 | 0.67 0.92 | <0.0001 | 0.2143 | 0.4444 |
| Other NSCLC | 0.804 | 0.68 0.93 | <0.0001 | 0.3333 | 0.1316 |
| SCC* | 0.790 | 0.62 0.96 | 0.0004 | 0.1538 | 0.1579 |

ADC: Adenocarcinoma;
SCC: Squamous cell carcinoma;
NSCLC, non-small cell lung cancer The discriminative performance of the biomarker score in the validation study yielded an AUC of 0.89 (95% CI: 0.84-0.93). the smoking model at an AUC of 0.79 (95% CI: 0.73-0.85, with a P value for the difference between the two estimates 0.002, FIG. 1, Table 6. The AUC for the biomarker score was consistently higher than that for the smoking model across relevant strata, varying between 0.83 for former smokers and 0.93 for light smokers (subjects with less than 30 pack-years of smoking history, Table 8). Combining the biomarker score with the smoking model in the integrated risk prediction model did not notably improve the AUC compared with the biomarker score alone (AUC for integrated risk prediction model: 0.90, 95% CI: 0.86-0.94, FIG. 1).

The discriminative performances of the smoking-model, the biomarker score, and the integrated risk prediction model were evaluated using ROC analyses in the validation study. In order to estimate the fraction of future lung cancer cases that would have been identified using the different models, we estimated the sensitivity of each model at a specificity level corresponding to that provided by applying the USPSTF screening eligibility criteria to each subject in the validation study. Conversely, we also evaluated the model specificity at the level of sensitivity obtained using the USPSTF criteria in order to estimate the extent to which screening could be avoided for subjects not destined develop lung cancer.

Application of the dichotomous USPSTF screening criteria to the validation study resulted in a sensitivity of 0.37 (95% CI: 0.23-0.48) and a specificity of 0.85 (95% CI: 0.72-0.91) (Table 8). The biomarker score at the specificity of the USPSTF screening criteria of 0.85, yielded a sensitivity of 0.78 (95% CI: 0.65-0.87) whereas the smoking model yielded a sensitivity of 0.58 (95% CI: 0.31-0.71). The sensitivity of the biomarker score varied between 0.65 and 0.85 across the strata (Table 8). In comparison, the sensitivity of the smoking model at the same specificity varied between 0.12 and 0.73 across the strata. We also evaluated the potential for improve specificity compared to the USPTSF criteria, with a view to avoid screening of subjects who are unlikely to develop lung cancer. At the overall sensitivity of 0.37 based on the USPSTF criteria, the corresponding specificity in the validation study using the biomarker score was 0.98 (95% CI: 0.96-1.00), compared to 0.90 (95% CI: 0.84-0.94) for the smoking model. The specificity of the biomarker score varied between 0.96 and 1.00 across strata and was consistently and notably higher than that of the smoking model for current smokers (Tables 3 and 9).

TABLE 8

Performance of 4-marker panel in CARET cohort.

| | Cases | Controls | Specificity of USPSTF criteria | 95% CI | Sensitivity of USPSTF criteria | 95% CI | Risk model |
|---|---|---|---|---|---|---|---|
| All | 83 | 158 | 0.85 | [0.72-0.91] | 0.37 | [0.23-0.48] | Smoking |
| | | | | | | | Biomarkers |
| | | | | | | | Smoking + Biomarkers |
| Men | 50 | 93 | 0.80 | [0.61-0.88] | 0.53 | [0.33-0.67] | Smoking |
| | | | | | | | Biomarkers |
| | | | | | | | Smoking + Biomarkers |
| Women | 33 | 65 | 0.92 | [0.8-0.98] | 0.13 | [0.03-0.26] | Smoking |
| | | | | | | | Biomarkers |
| | | | | | | | Smoking + Biomarkers |
| Never smokers | 9 | 50 | N/A | | N/A | | Smoking |
| | | | | | | | Biomarkers |
| | | | | | | | Smoking + Biomarkers |
| Former smokers | 26 | 53 | 0.90 | [0.71-0.97] | 0.29 | [0.1-0.48] | Smoking |
| | | | | | | | Biomarkers |
| | | | | | | | Smoking + Biomarkers |
| Current smokers | 48 | 55 | 0.67 | [0.49-0.81] | 0.48 | [0.3-0.63] | Smoking |
| | | | | | | | Biomarkers |
| | | | | | | | Smoking + Biomarkers |
| NSCLC Cases | 70 | 158 | 0.85 | [0.72-0.91] | 0.35 | [0.21-0.47] | Smoking |
| | | | | | | | Biomarkers |
| | | | | | | | Smoking + Biomarkers |
| Heavy smokers | 25 | 19 | N/A | | N/A | | Smoking |
| | | | | | | | Biomarkers |
| | | | | | | | Smoking + Biomarkers |
| Light smokers | 23 | 36 | N/A | | N/A | | Smoking |
| | | | | | | | Biomarkers |
| | | | | | | | Smoking + Biomarkers |

| | AUC | 95% CI | Sensitivity at USPSTF Specificity | 95% CI | Specificity at USPSTF Sensitivity | 95% CI |
|---|---|---|---|---|---|---|
| All | 0.79 | [0.73-0.85] | 0.58 | [0.31-0.71] | 0.90 | [0.84-0.94] |
| | 0.89 | [0.84-0.93] | 0.78 | [0.65-0.87] | 0.98 | [0.96-1.00] |
| | 0.90 | [0.86-0.94] | 0.80 | [0.70-0.89] | 0.97 | [0.95-1.00] |
| Men | 0.84 | [0.77-0.90] | 0.72 | [0.56-0.84] | 0.94 | [0.84-0.98] |
| | 0.87 | [0.81-0.94] | 0.76 | [0.64-0.90] | 0.98 | [0.90-1.00] |
| | 0.89 | [0.84-0.95] | 0.82 | [0.70-0.94] | 0.96 | [0.90-1.00] |
| Women | 0.71 | [0.61-0.82] | 0.12 | [0.00-0.30] | 0.89 | [0.77-0.98] |
| | 0.91 | [0.84-0.97] | 0.70 | [0.52-0.88] | 1.00 | [0.97-1.00] |
| | 0.91 | [0.85-0.97] | 0.67 | [0.48-0.88] | 0.98 | [0.95-1.00] |
| Never smokers | N/A | | N/A | | N/A | |
| | 0.89 | [0.71-1.00] | N/A | | N/A | |
| | N/A | | N/A | | N/A | |
| Former smokers | 0.81 | [0.70-0.91] | 0.58 | [0.23-0.77] | 0.96 | [0.89-1.00] |
| | 0.83 | [0.73-0.93] | 0.65 | [0.31-0.85] | 0.96 | [0.89-1.00] |
| | 0.87 | [0.79-0.95] | 0.69 | [0.35-0.88] | 0.96 | [0.91-1.00] |
| Current smokers | 0.69 | [0.59-0.79] | 0.73 | [0.31-0.85] | 0.75 | [0.60-0.85] |
| | 0.88 | [0.82-0.95] | 0.85 | [0.75-0.98] | 0.98 | [0.93-1.00] |
| | 0.88 | [0.81-0.95] | 0.88 | [0.77-0.98] | 0.96 | [0.89-1.00] |
| NSCLC Cases | 0.78 | [0.72-0.84] | 0.54 | [0.29-0.69] | 0.90 | [0.84-0.94] |
| | 0.88 | [0.83-0.93] | 0.77 | [0.64-0.86] | 0.98 | [0.96-1.00] |
| | 0.90 | [0.85-0.94] | 0.79 | [0.69-0.89] | 0.98 | [0.96-1.00] |
| Heavy smokers | 0.65 | [0.49-0.82] | N/A | | | |
| | 0.84 | [0.72-0.96] | N/A | | | |
| | 0.83 | [0.70-0.95] | N/A | | | |
| Light smokers | 0.69 | [0.55-0.83] | | | | |
| | 0.93 | [0.87-0.99] | | | | |
| | 0.92 | [0.85-0.99] | | | | |

TABLE 9

Discriminative Performance of three risk prediction models in the validation study among ever smokers

| | Cases | Controls | Specificity of USPSTF criteria | 95% CI | Sensitivity of USPSTF criteria | 95% CI | Risk model |
|---|---|---|---|---|---|---|---|
| All | 71 | 103 | 0.77 | [0.62-0.86] | 0.41 | [0.26-0.53] | Smoking<br>Biomarkers<br>Smoking + Biomarkers |
| Men | 44 | 69 | 0.73 | [0.51-0.84] | 0.58 | [0.37-0.72] | Smoking<br>Biomarkers<br>Smoking + Biomarkers |
| Women | 27 | 34 | 0.85 | [0.7-0.97] | 0.12 | [0.02-0.28] | Smoking<br>Biomarkers<br>Smoking + Biomarkers |
| Former smokers | 25 | 50 | 0.89 | [0.7-0.97] | 0.30 | [0.11-0.49] | Smoking<br>Biomarkers<br>Smoking + Biomarkers |
| Current smokers | 46 | 53 | 0.66 | [0.49-0.8] | 0.46 | [0.28-0.62] | Smoking<br>Biomarkers<br>Smoking + Biomarkers |
| NSCLC Cases | 58 | 103 | 0.77 | [0.61-0.86] | 0.39 | [0.23-0.53] | Smoking<br>Biomarkers<br>Smoking + Biomarkers |
| Heavy smokers | 23 | 18 | N/A | | N/A | | Smoking<br>Biomarkers<br>Smoking + Biomarkers |
| Light smokers | 20 | 35 | N/A | | N/A | | Smoking<br>Biomarkers<br>Smoking + Biomarkers |

| | AUC | 95% CI | Sensitivity at USPSTF Specificity | 95% CI | Specificity at USPSTF Sensitivity | 95% CI |
|---|---|---|---|---|---|---|
| All | 0.77 | [0.70-0.84] | 0.58 | [0.42-0.73] | 0.88 | [0.79-0.96] |
| | 0.86 | [0.81-0.92] | 0.75 | [0.63-0.89] | 0.97 | [0.92-1.00] |
| | 0.88 | [0.83-0.93] | 0.85 | [0.69-0.94] | 0.95 | [0.90-0.99] |
| Men | 0.83 | [0.75-0.90] | 0.77 | [0.59-0.91] | 0.87 | [0.74-0.94] |
| | 0.87 | [0.80-0.93] | 0.75 | [0.61-0.93] | 0.96 | [0.81-1.00] |
| | 0.89 | [0.83-0.95] | 0.89 | [0.73-0.98] | 0.96 | [0.88-1.00] |
| Women | 0.63 | [0.49-0.77] | 0.26 | [0.07-0.48] | 0.94 | [0.76-1.00] |
| | 0.86 | [0.77-0.96] | 0.70 | [0.48-0.93] | 0.97 | [0.91-1.00] |
| | 0.87 | [0.78-0.96] | 0.81 | [0.33-0.96] | 0.94 | [0.85-1.00] |
| Former smokers | 0.83 | [0.72-0.93] | 0.56 | [0.32-0.80] | 0.96 | [0.90-1.00] |
| | 0.84 | [0.74-0.93] | 0.64 | [0.40-0.80] | 0.98 | [0.92-1.00] |
| | 0.89 | [0.82-0.97] | 0.68 | [0.40-0.92] | 0.98 | [0.90-1.00] |
| Current smokers | 0.70 | [0.59-0.80] | 0.61 | [0.41-0.80] | 0.79 | [0.62-0.91] |
| | 0.88 | [0.81-0.95] | 0.89 | [0.74-1.00] | 0.94 | [0.89-1.00] |
| | 0.87 | [0.80-0.94] | 0.91 | [0.76-0.98] | 0.94 | [0.87-1.00] |
| NSCLC Cases | 0.77 | [0.69-0.84] | 0.59 | [0.41-0.74] | 0.90 | [0.80-0.97] |
| | 0.86 | [0.80-0.92] | 0.76 | [0.64-0.88] | 0.98 | [0.94-1.00] |
| | 0.88 | [0.82-0.93] | 0.81 | [0.67-0.91] | 0.95 | [0.91-0.99] |
| Heavy smokers | 0.65 | [0.48-0.83] | | | | |
| | 0.86 | [0.74-0.97] | | | | |
| | 0.86 | [0.75-0.97] | | | | |
| Light smokers | 0.73 | [0.60-0.86] | | | | |
| | 0.91 | [0.83-0.98] | | | | |
| | 0.89 | [0.80-0.97] | | | | |

Figure 2:
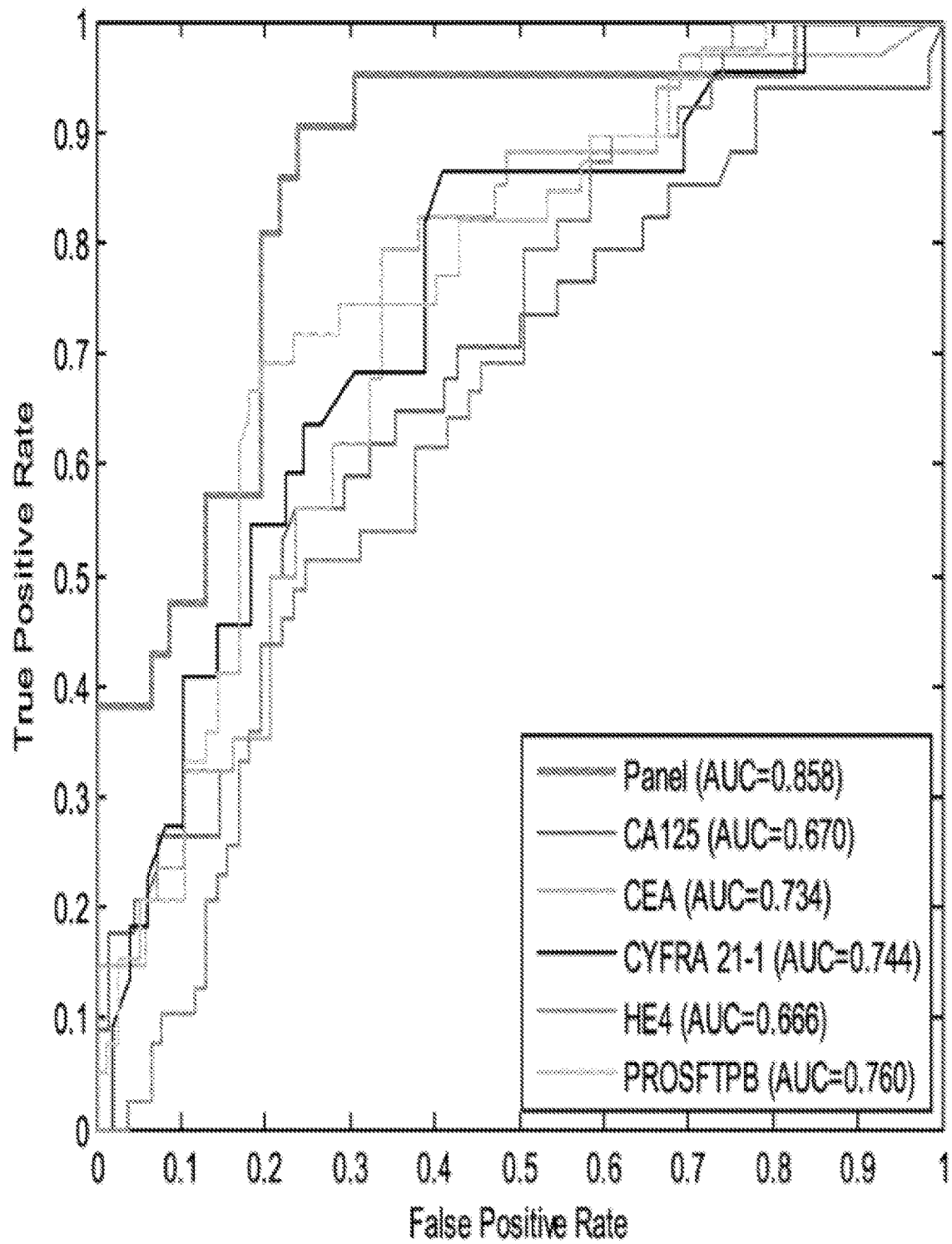
FIG. 2 depicts ROC curves for all 5 biomarkers in CARET along with the 4 marker panel for 0-6 months from diagnosis.
Figure 3:
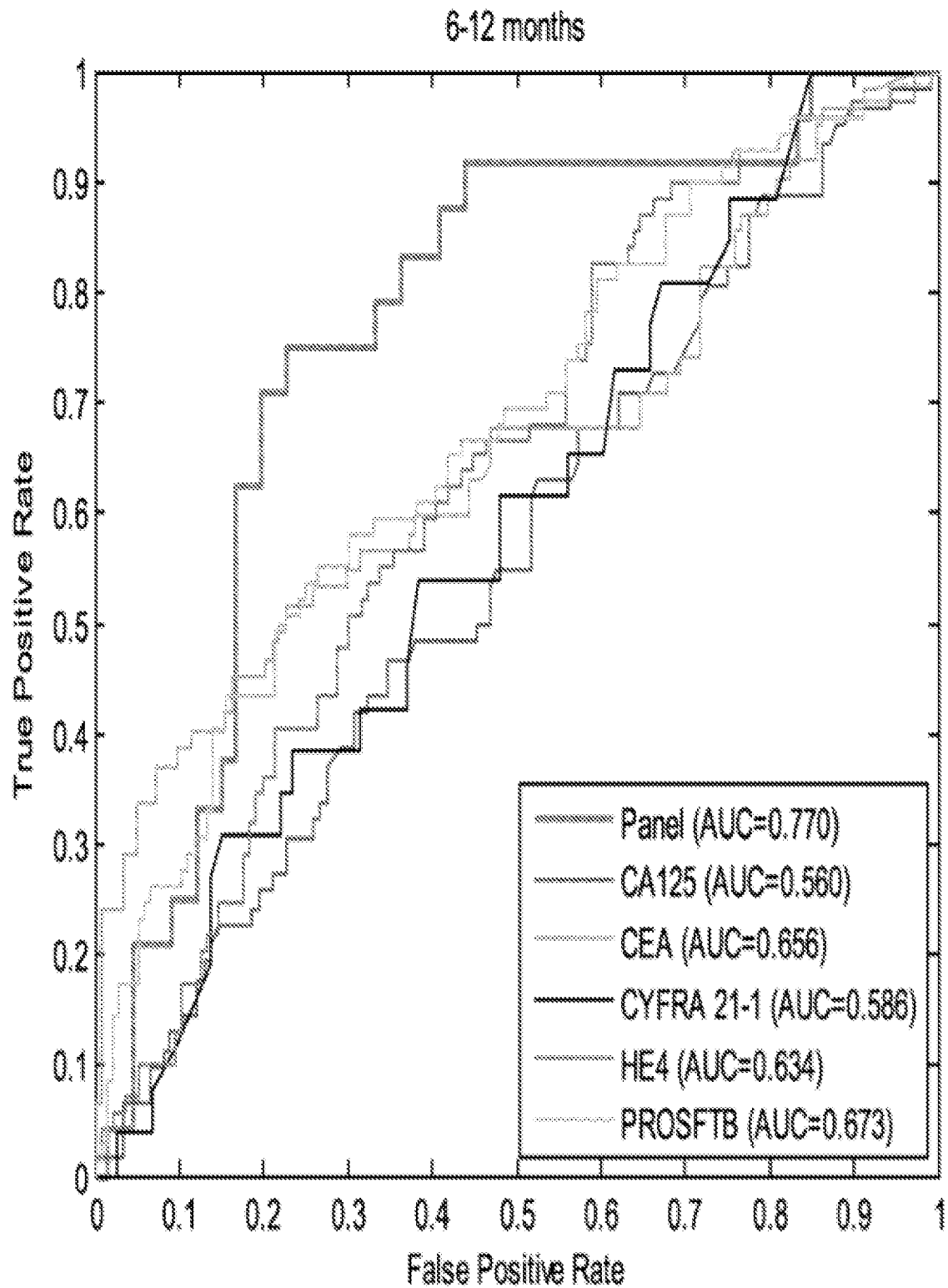
FIG. 3 depicts ROC curves for all 5 biomarkers in CARET along with the 4 marker panel for ≥6-12 months from diagnosis.

The sensitivity of the panel at 95% specificity was 38% for subjects who were diagnosed with lung cancer within 6 months of blood draw (FIG. 2) and 21% for subjects who developed lung cancer more than 6 months and up to 12 months following blood draw (FIG. 3) (AUC=0.858, 95% CI: 0.76-0.96; AUC=0.770, 95% CI: 0.66-0.88, respectively). The panel offered comparable classification for the two most prevalent histologic types of lung cancer: an AUC of 0.794 for lung adenocarcinoma (95% CI: 0.67-0.92; SN=21%, SP=95%), an AUC of 0.790 in lung squamous carcinoma (95% CI: 0.62-0.96; SN=15%, SP=95%). The remainder of NSCLC were classified with an AUC of 0.804 (95% CI: 0.68-0.93) with a sensitivity of 33% (SP=95%). Panel performance for females was (AUC-0.829; 95% CI: 0.70-0.96) and males (AUC=0.783; 95% CI: 0.69-0.88).

The extent to which the biomarker-score could discriminate between incident lung cancer cases and controls was evaluated externally and non-parametrically by combining EPIC and NSHDS samples and assigning each participant the biomarker-score, and evaluating the performance using receiver-operating characteristics (ROC) curve analyses.

The biomarker-score was evaluated for its potential to improve a risk prediction model based on smoking variables alone using the combined EPIC and NSHDS sample, first by fitting a model (smoking model) including smoking variables using unconditional logistic regression. This model included age (continuous), sex (dichotomous), cohort (dichotomous), smoking status (former/current), cigarettes per day in current smokers (continuous [not available in former smokers]), smoking duration (continuous), and time since quitting in former smokers (continuous). Subsequently, an integrated risk prediction model was determined by fitting a new model also including the biomarker-score with the smoking model. The discriminative performance of the integrated risk prediction model compared to the smoking model was primarily evaluated by analyzing the EPIC and NSHDS samples combined.

In order to estimate the fraction of future lung cancer cases that would have been identified using the different models, the sensitivity of each model at a specificity corresponding to that provided by applying the USPSTF screening eligibility criteria was set. Conversely, the model specificity was also examined at the USPSTF sensitivity in order to estimate the extent to which screening could be avoided in subjects who will not develop lung cancer.

In ROC analysis, the overall performance of the smoking model (demographic and questionnaire-based smoking variables only) in discriminating cases and controls in the combined EPIC and NSHDS validation sample was estimated at an AUC of 0.72 (95% CI: 0.65-0.79, FIG. 1). The corresponding discriminative performance of the biomarker-score alone was estimated at an AUC of 0.80 (95% CI: 0.74-0.87, p-value comparing the AUC with the smoking model: 0.07). Combining the biomarker-score with the smoking model in the integrated risk prediction model resulted in an AUC of 0.83 (95% CI: 0.77-0.89, p-value comparing the AUC with the smoking model: 0.001).

The AUC estimate afforded by the integrated risk prediction model was similar when stratifying by sex and smoking status (range: 0.79 to 0.84), but higher in study participants who smoked less than 30 pack-years of cigarettes (AUC: 0.90, 95% CI: 0.83-0.96) compared to study participants who smoked more than 30 pack-years (AUC: 0.67, 95% CI: 0.53-0.81, p-value: 0.0053).

Applying the dichotomous USPSTF screening criteria on the validation sample resulted in an overall sensitivity of 0.42 (95% CI: 0.26-0.54) and a specificity of 0.78 (95% CI: 0.64-0.87). In order to evaluate the potential of improving the sensitivity when referring future lung cancer cases to screening—as opposed to applying the currently used USPSTF criteria—the sensitivity of the integrated risk prediction model at the specificity of the USPSTF criteria was evaluated. Accordingly, at a specificity of 0.78, the sensitivity for the integrated risk prediction model was 0.76 (95% CI: 0.57-0.86) and varied between 0.61 and 0.83 across the strata, but was consistently higher than that of the USPSTF criterion (Table 9). In comparison, the overall sensitivity of the smoking model at the same specificity was 0.41 (95% CI: 0.28-0.66) and varied between 0.21 and 0.57 across the strata. Conversely, studies were undertaken to improve the specificity of the USPTSF criteria, with the view to avoid referring subjects who will not develop lung cancer for screening. Here, at the overall sensitivity of 0.42—that of the USPSTF criteria—the corresponding specificity using the integrated risk prediction model was 0.94 (95% CI: 0.88-0.98), as opposed to 0.78 (95% CI: 0.70-0.90) of the smoking model. Again, the specificity of the integrated risk prediction model was consistently and notably higher than that of the smoking model and varied between 0.88 and 1.00 across strata.

Example 6: Expansion of Panel with Additional Biomarkers

In an exploratory analysis, 16 additional promising biomarkers were also analyzed against the validation cohort to evaluate their potential in risk prediction. Based on data on these 16 biomarkers, further improvement to the discriminative performance of the biomarker-score developed in CARET was pursued. Based on penalized logistic regression (lasso), 2 additional biomarkers were selected from the 16 assayed biomarkers in addition to the biomarker score, resulting in a nominally higher AUC of 0.83 (95% CI: 0.77-0.90) overall, as compared to 0.80 (95% CI: 0.74-0.87) of the biomarker score alone (p-value: 0.11). The bootstrap-optimism corrected AUC estimate was 0.80, indicating that the potential of the additional 16 biomarkers to further improve lung cancer risk prediction is limited.

Example 7: Specificity and Sensitivity in the Range of Regression Model Diagnostic Scores It will be appreciated by those of ordinary skill in the art that different methods or assays of biomarker detection, quantitation, and analysis, which can include using different reagents, will produce different results which may require modification of the regression model. In particular, different assays can produce results expressed, for example, in different units. Further, duplicate reactions in duplicate assays of the same samples can also produce different raw results. However, it is the combined detection, quantitation, and analysis of at least the four biomarkers CEA, CA125, CYFRA21-1, and Pro-SFTPB that, when incorporated into a regression model as disclosed herein, produce a definitive diagnosis of lung cancer.

A range in the results reported for each particular assay used to detect, quantify, and analyze the four biomarkers will have a range in the resulting lung cancer-predictive score that depends, in part, on the degree of sensitivity or specificity (Table 10; where the preferred cutoff based on the Youden Index is-1.073 with a specificity of 0.714 and sensitivity of 0.822). The regression model used to generate the lung cancer-predictive score can dependent on the specific assays utilized to test the markers. As understood by those of skill in the art, different assays can target different epitopes of the four biomarkers or have different affinities and sensitivities. As such, the regression model algorithm used to generate the lung cancer-predictive score can be modified to take these assay variations into consideration.

Example 8: Assaying Samples and Lung Cancer-Patient Diagnosis

In one example, a patient being screened for lung cancer—based on the four-biomarker panel disclosed herein—has a blood sample drawn (or other fluid or tissue biopsy) and assayed by ELISA (or other assay) to quantitate the levels of CEA, CA125, CYFRA21-1, and Pro-SFTPB in the patient. Normalized values for at least these biomarkers that take into account the specific assay used could be, for example, CEA=3.2 ng/ml; CA125=3.5 U/mL; CYFRA21-1=2.1 ng/ml; and Pro-SFTPB=6 ng/mL. Raw assay data are then log 2-transformed, computing the mean and standard deviation for the healthy samples in each cohort. The data is then standardized so that healthy samples have a mean of 0 and a standard deviation of 1: where (Readj−meanhealthy)/(stdhealthy), where j is the jth sample.

When analyzed using the following regression model:

$$\log it(p) = -8.4927 + 0.4730 \times \log CA125 + 0.2612 \times \log CYFRA211 + 0.6531 \times \log CEA$$

the above patient would have a combined score of 1.344. In view of the preferred cutoff for consideration of both specificity and sensitivity (Table 10), a patient with such a combined score would have lung cancer with near certainty and consequently be directed for follow-up testing and treatment for lung cancer using other modalities discussed herein and known to those of skill in the art. Using the regression model described herein, the more positive the combined lung cancer-predictive score, the more certainty the patient has lung cancer. Conversely, the more negative the combined lung cancer-predictive score, the more certainty the patient does not have lung cancer.

By contrast, in another example, normalized values for biomarkers CEA, CA125, CYFRA21-1, and Pro-SFTPB that take into account the specific assay used could be, for example, CEA=0.1 ng/ml; CA125=2.0 U/mL; CYFRA21-1=−1.2 ng/ml; and Pro-SFTPB=4.0 ng/mL. When analyzed using the same regression model as above, such a patient would have a combined score of −4.3347. In view of the preferred cutoff for consideration of both specificity and sensitivity (Table 10), a patient with such a combined score would, with near certainty, not have lung cancer and, therefore, would or would not need to be followed for additional testing based on the strength of any other clinical conditions.

TABLE 10

Sensitivity and specificity at different cutoffs of the biomarker panel-based (CEA, CA125, CYFRA21-1 and Pro-SFTPB) scores in the combination validation set.

| Cutoff | Specificity | Sensitivity | Youden |
|---|---|---|---|
| 2.252 | 1.000 | 0.000 | 0.000 |
| 2.252 | 1.000 | 0.022 | 0.022 |
| 1.978 | 1.000 | 0.044 | 0.044 |
| 1.942 | 1.000 | 0.067 | 0.067 |
| 1.925 | 1.000 | 0.089 | 0.089 |
| 1.693 | 1.000 | 0.111 | 0.111 |
| 1.560 | 1.000 | 0.133 | 0.133 |
| 1.548 | 1.000 | 0.156 | 0.156 |
| 1.120 | 1.000 | 0.178 | 0.178 |
| 0.786 | 0.991 | 0.178 | 0.169 |
| 0.786 | 0.991 | 0.200 | 0.191 |
| 0.779 | 0.982 | 0.200 | 0.182 |
| 0.579 | 0.973 | 0.200 | 0.173 |
| 0.546 | 0.964 | 0.200 | 0.164 |
| 0.526 | 0.955 | 0.200 | 0.155 |
| 0.507 | 0.946 | 0.200 | 0.146 |
| 0.464 | 0.946 | 0.222 | 0.169 |
| 0.426 | 0.946 | 0.244 | 0.191 |
| 0.407 | 0.938 | 0.244 | 0.182 |
| 0.400 | 0.938 | 0.267 | 0.204 |
| 0.357 | 0.938 | 0.289 | 0.226 |
| 0.249 | 0.938 | 0.311 | 0.249 |
| 0.230 | 0.929 | 0.311 | 0.240 |
| 0.191 | 0.920 | 0.311 | 0.231 |
| 0.138 | 0.920 | 0.333 | 0.253 |
| 0.120 | 0.920 | 0.356 | 0.275 |
| 0.083 | 0.911 | 0.356 | 0.266 |
| 0.053 | 0.911 | 0.378 | 0.288 |
| 0.037 | 0.902 | 0.378 | 0.280 |
| −0.019 | 0.893 | 0.378 | 0.271 |
| −0.027 | 0.884 | 0.378 | 0.262 |
| −0.030 | 0.875 | 0.378 | 0.253 |
| −0.043 | 0.866 | 0.378 | 0.244 |
| −0.052 | 0.866 | 0.400 | 0.266 |
| −0.055 | 0.866 | 0.422 | 0.288 |
| −0.098 | 0.866 | 0.444 | 0.311 |
| −0.127 | 0.866 | 0.467 | 0.333 |
| −0.169 | 0.857 | 0.467 | 0.324 |
| −0.174 | 0.857 | 0.489 | 0.346 |
| −0.197 | 0.857 | 0.511 | 0.368 |
| −0.231 | 0.848 | 0.511 | 0.359 |
| −0.233 | 0.839 | 0.511 | 0.350 |
| −0.257 | 0.839 | 0.533 | 0.373 |
| −0.302 | 0.839 | 0.556 | 0.395 |
| −0.348 | 0.830 | 0.556 | 0.386 |
| −0.404 | 0.830 | 0.578 | 0.408 |
| −0.466 | 0.830 | 0.600 | 0.430 |
| −0.491 | 0.821 | 0.600 | 0.421 |
| −0.515 | 0.813 | 0.600 | 0.413 |
| −0.521 | 0.804 | 0.600 | 0.404 |
| −0.552 | 0.795 | 0.600 | 0.395 |
| −0.586 | 0.795 | 0.622 | 0.417 |
| −0.629 | 0.786 | 0.622 | 0.408 |
| −0.692 | 0.777 | 0.622 | 0.399 |
| −0.700 | 0.777 | 0.644 | 0.421 |
| −0.707 | 0.777 | 0.667 | 0.443 |
| −0.708 | 0.777 | 0.689 | 0.466 |
| −0.735 | 0.777 | 0.711 | 0.488 |
| −0.773 | 0.768 | 0.711 | 0.479 |
| −0.794 | 0.768 | 0.733 | 0.501 |
| −0.796 | 0.768 | 0.756 | 0.523 |
| −0.822 | 0.759 | 0.756 | 0.514 |
| −0.930 | 0.750 | 0.756 | 0.506 |
| −0.949 | 0.750 | 0.778 | 0.528 |
| −0.994 | 0.741 | 0.778 | 0.519 |
| −1.033 | 0.732 | 0.778 | 0.510 |
| −1.055 | 0.723 | 0.778 | 0.501 |
| −1.065 | 0.714 | 0.778 | 0.492 |
| −1.066 | 0.714 | 0.800 | 0.514 |
| −1.073 | 0.714 | 0.822 | 0.537 |
| −1.084 | 0.705 | 0.822 | 0.528 |
| −1.093 | 0.696 | 0.822 | 0.519 |
| −1.101 | 0.688 | 0.822 | 0.510 |
| −1.121 | 0.679 | 0.822 | 0.501 |
| −1.145 | 0.679 | 0.844 | 0.523 |
| −1.157 | 0.670 | 0.844 | 0.514 |
| −1.168 | 0.661 | 0.844 | 0.505 |
| −1.168 | 0.652 | 0.844 | 0.496 |
| −1.186 | 0.643 | 0.844 | 0.487 |
| −1.186 | 0.634 | 0.844 | 0.478 |
| −1.194 | 0.625 | 0.844 | 0.469 |
| −1.306 | 0.616 | 0.844 | 0.461 |
| −1.339 | 0.607 | 0.844 | 0.452 |
| −1.378 | 0.598 | 0.844 | 0.443 |
| −1.384 | 0.598 | 0.867 | 0.465 |
| −1.390 | 0.589 | 0.867 | 0.456 |
| −1.399 | 0.580 | 0.867 | 0.447 |
| −1.401 | 0.571 | 0.867 | 0.438 |
| −1.407 | 0.563 | 0.867 | 0.429 |
| −1.438 | 0.563 | 0.889 | 0.451 |
| −1.447 | 0.554 | 0.889 | 0.442 |
| −1.449 | 0.545 | 0.889 | 0.434 |
| −1.459 | 0.536 | 0.889 | 0.425 |
| −1.464 | 0.527 | 0.889 | 0.416 |
| −1.470 | 0.518 | 0.889 | 0.407 |
| −1.551 | 0.518 | 0.911 | 0.429 |
| −1.556 | 0.509 | 0.911 | 0.420 |
| −1.612 | 0.500 | 0.911 | 0.411 |
| −1.614 | 0.500 | 0.933 | 0.433 |
| −1.626 | 0.491 | 0.933 | 0.424 |
| −1.627 | 0.482 | 0.933 | 0.415 |
| −1.631 | 0.473 | 0.933 | 0.407 |
| −1.672 | 0.464 | 0.933 | 0.398 |
| −1.694 | 0.455 | 0.933 | 0.389 |
| −1.769 | 0.446 | 0.933 | 0.380 |
| −1.772 | 0.438 | 0.933 | 0.371 |

TABLE 10-continued

Sensitivity and specificity at different cutoffs of the biomarker panel-based (CEA, CA125, CYFRA21-1 and Pro-SFTPB) scores in the combination validation set.

| Cutoff | Specificity | Sensitivity | Youden |
|---|---|---|---|
| −1.816 | 0.429 | 0.933 | 0.362 |
| −1.826 | 0.420 | 0.933 | 0.353 |
| −1.846 | 0.411 | 0.933 | 0.344 |
| −1.864 | 0.402 | 0.933 | 0.335 |
| −1.872 | 0.393 | 0.933 | 0.326 |
| −1.882 | 0.384 | 0.933 | 0.317 |
| −1.895 | 0.375 | 0.933 | 0.308 |
| −1.921 | 0.366 | 0.933 | 0.299 |
| −1.960 | 0.357 | 0.933 | 0.290 |
| −2.021 | 0.348 | 0.933 | 0.282 |
| −2.143 | 0.339 | 0.933 | 0.273 |
| −2.180 | 0.330 | 0.933 | 0.264 |
| −2.189 | 0.321 | 0.933 | 0.255 |
| −2.201 | 0.313 | 0.933 | 0.246 |
| −2.211 | 0.304 | 0.933 | 0.237 |
| −2.212 | 0.295 | 0.933 | 0.228 |
| −2.259 | 0.286 | 0.933 | 0.219 |
| −2.306 | 0.277 | 0.933 | 0.210 |
| −2.389 | 0.268 | 0.933 | 0.201 |
| −2.454 | 0.259 | 0.933 | 0.192 |
| −2.479 | 0.250 | 0.933 | 0.183 |
| −2.485 | 0.241 | 0.933 | 0.174 |
| −2.502 | 0.232 | 0.933 | 0.165 |
| −2.511 | 0.223 | 0.933 | 0.157 |
| −2.556 | 0.214 | 0.933 | 0.148 |
| −2.569 | 0.205 | 0.933 | 0.139 |
| −2.588 | 0.196 | 0.933 | 0.130 |
| −2.589 | 0.188 | 0.933 | 0.121 |
| −2.619 | 0.188 | 0.956 | 0.143 |
| −2.755 | 0.179 | 0.956 | 0.134 |
| −2.806 | 0.170 | 0.956 | 0.125 |
| −2.845 | 0.161 | 0.956 | 0.116 |
| −2.870 | 0.152 | 0.956 | 0.107 |
| −2.873 | 0.152 | 0.978 | 0.130 |
| −2.966 | 0.143 | 0.978 | 0.121 |
| −2.976 | 0.134 | 0.978 | 0.112 |
| −3.031 | 0.134 | 1.000 | 0.134 |
| −3.039 | 0.125 | 1.000 | 0.125 |
| −3.051 | 0.116 | 1.000 | 0.116 |
| −3.083 | 0.107 | 1.000 | 0.107 |
| −3.231 | 0.098 | 1.000 | 0.098 |
| −3.262 | 0.089 | 1.000 | 0.089 |
| −3.414 | 0.080 | 1.000 | 0.080 |
| −3.521 | 0.071 | 1.000 | 0.071 |
| −3.645 | 0.063 | 1.000 | 0.063 |
| −3.705 | 0.054 | 1.000 | 0.054 |
| −3.774 | 0.045 | 1.000 | 0.045 |
| −3.882 | 0.036 | 1.000 | 0.036 |
| −3.936 | 0.027 | 1.000 | 0.027 |
| −4.225 | 0.018 | 1.000 | 0.018 |
| −4.356 | 0.009 | 1.000 | 0.009 |
| −4.595 | 0.000 | 1.000 | 0.000 |

Example 9: Additive Effect of Metabolite and Protein Markers

Figure 4:
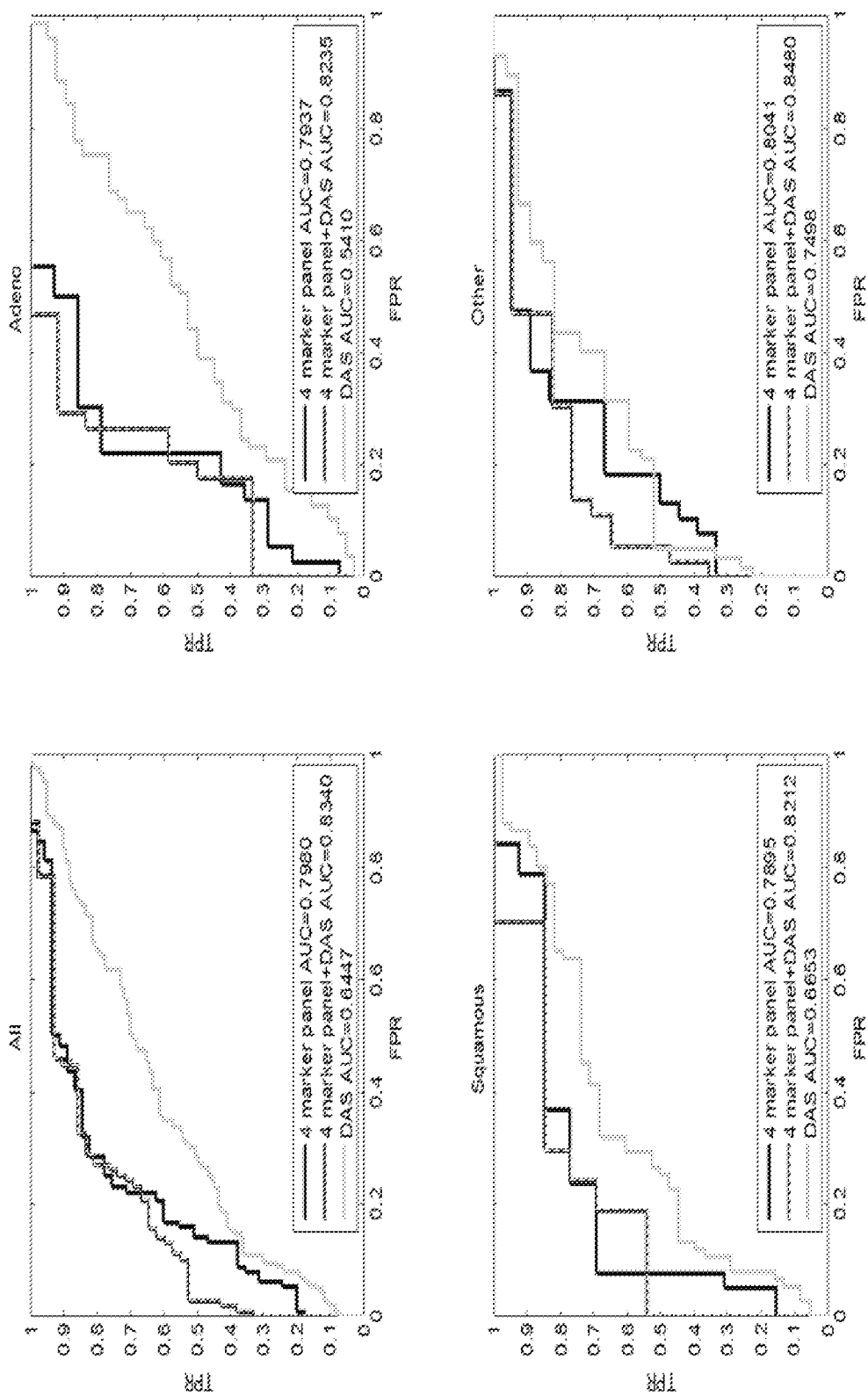
FIG. 4 depicts ROC curves for the 4-marker panel (dark grey line), the 4-marker panel with the addition of diacetylspermine (DAS) (dotted line), and DAS alone (light grey line) for all samples analyzed (top left panel), adenocarcinoma samples (top right panel), squamous cell lung cancer (bottom left panel), and samples other than squamous cell lung cancer and adenocarcinoma (bottom right panel).

An investigation was performed to evaluate the contribution of adding a metabolite such as di-acetyl spermine (DAS), which was previously identified as a marker for non small-cell lung cancer, to the four-marker lung cancer panel. The data indicated an additive performance, particularly in non-adenocarcinoma cases (FIG. 4).

The combination of metabolite and protein markers in pre-diagnostic blood samples from a group of 100 lung cancer cases and twice as many controls showed improved performance compared to the four-marker panel alone, with particularly improved performance for subjects that were subsequently diagnosed with squamous lung cancer or with other than squamous or adenocarcinoma. Therefore, the addition of a metabolite marker such as DAS to a panel of protein markers allows for improved early detection for lung cancer compared to protein markers alone.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method comprising
   (a) obtaining a biological sample from a subject;
   (b) measuring levels of biomarkers in the sample, wherein the biomarkers comprise CEA, CA125, CYFRA21-1, and PRO-SFTPB;
   (c) combining the measured levels into a biomarker-based risk score, wherein the biomarker-based risk score is calculated using logistic regression analysis;
   (d) quantifying an increased risk for the presence of lung cancer in the subject by matching the biomarker-based risk score to a risk category of a grouping of stratified subject populations, wherein each risk category comprises a multiplier indicating increased likelihood of having lung cancer correlated to a range of composite scores as compared to use of a single threshold value;
   (e) classifying the subject as lung-cancer positive based on the increased risk of having lung cancer quantified in step (d); and
   (f) administering to the lung-cancer positive subject a therapeutically effective amount of a treatment for the lung cancer comprising surgery, chemotherapy, immunotherapy, radiation therapy, targeted therapy, or a combination thereof.

2. The method of claim 1, wherein the sample comprises a biological sample selected from blood, plasma, and serum.

3. The method of claim 1, wherein measurement of the levels of CEA, CA125, CYFRA21-1, and pro-SFTPB levels is made at substantially the same time.

4. The method of claim 1, wherein the quantification of the increased risk for the presence of lung cancer has a sensitivity of 0.76 and 0.42 at 78% and 94% specificity, respectively.

5. The method of claim 1, wherein the quantification of the increased risk for the presence of lung cancer is diagnosed at or before the borderline resectable stage.

* * * * *